US012760092B2

(12) United States Patent
Callewaert et al.

(10) Patent No.: US 12,760,092 B2
(45) Date of Patent: Oct. 13, 2026

(54) GLYCOSYLATED SINGLE CHAIN IMMUNOGLOBULIN DOMAINS

(71) Applicants: VIB VZW, Ghent (BE); UNIVERSITEIT GENT, Ghent (BE)

(72) Inventors: Nico Callewaert, Nevele (BE); Loes Van Schie, Ghent (BE); Wander Van Breedam, Antwerp (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 1120 days.

(21) Appl. No.: 17/784,196

(22) PCT Filed: Dec. 10, 2020

(86) PCT No.: PCT/EP2020/085436
§ 371 (c)(1),
(2) Date: Jun. 10, 2022

(87) PCT Pub. No.: WO2021/116252
PCT Pub. Date: Jun. 17, 2021

(65) Prior Publication Data

US 2023/0062229 A1 Mar. 2, 2023

(30) Foreign Application Priority Data

Dec. 12, 2019 (GB) ..................................... 1918279

(51) Int. Cl.
*C07K 16/18* (2006.01)
*C12N 15/63* (2006.01)

(52) U.S. Cl.
CPC .............. *C07K 16/18* (2013.01); *C12N 15/63* (2013.01); *C07K 2317/22* (2013.01); *C07K 2317/41* (2013.01); *C07K 2317/569* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | | |
|---|---|---|---|---|
| 10,501,540 | B2 * | 12/2019 | Van Der Vliet | A61P 35/00 |
| 11,891,451 | B2 * | 2/2024 | Callewaert | C07K 16/40 |
| 2012/0276103 | A1 * | 11/2012 | Karperien | C07K 16/22 427/2.24 |
| 2018/0044407 | A1 * | 2/2018 | Buyse | C07K 16/18 |

FOREIGN PATENT DOCUMENTS

| | | | | |
|---|---|---|---|---|
| WO | WO-2011075861 | A1 * | 6/2011 | C07K 16/241 |
| WO | 2016150845 | A1 | 9/2016 | |
| WO | 2018206734 | A1 | 11/2018 | |

OTHER PUBLICATIONS

PCT International Search Report and Written Opinion; Application No. PCT/EP2020/85436 Vib Vzw, International filing date of Dec. 10, 2020, mailing date Dec. 12, 2019, 16 pages.
Harmsen, Michiel, et al., "Isolation of Panels of Llama Single-Domain Antibody Fragments Binding All Nine Neuraminidase Subtypes of Influenza A Virus," Antibodies, vol. 2, No. 4, Dec. 1, 2013, pp. 168-192.

* cited by examiner

*Primary Examiner* — Marianne P Allen
(74) *Attorney, Agent, or Firm* — Patent Law Works LLP

(57) ABSTRACT

The present application relates to glycosylated immunoglobulin domains. The invention provides nucleotide sequences encoding polypeptides comprising immunoglobulin variable domains with engineered glycosylation acceptor sites. Accordingly, the invention provides immunoglobulin variable domain proteins modified with selected glycans and specific glycan-conjugates thereof. Also provided herein are methods for the production of glycosylated immunoglobulin variable domains and glycan-conjugates thereof.

9 Claims, 9 Drawing Sheets
(8 of 9 Drawing Sheet(s) Filed in Color)
Specification includes a Sequence Listing.

GLYCOSYLATED SINGLE CHAIN IMMUNOGLOBULIN DOMAINS

CROSS REFERENCE TO RELATED APPLICATIONS

This application is a national phase entry under 35 U.S.C. § 371 of International Patent Application PCT/EP2020/085436, filed Dec. 10, 2020, designating the United States of America and published in English as International Patent Publication WO 2021/116252 on Jun. 17, 2021, which claims the benefit under Article 8 of the Patent Cooperation Treaty to United Kingdom Patent Application Serial No. 1918279.9, filed Dec. 12, 2019, the entireties of which are hereby incorporated by reference.

FIELD OF THE INVENTION

The present application relates to the field of glycosylation engineering, more particularly to immunoglobulin domains and glycosylated derivatives thereof. In particular, the invention provides nucleotide sequences encoding polypeptides comprising immunoglobulin variable domains with engineered glycosylation acceptor sites. Accordingly, the invention provides immunoglobulin variable domain proteins modified with selected glycans and specific glycan-conjugates thereof. Also provided herein are methods for the production of glycosylated immunoglobulin variable domains and glycan-conjugates thereof.

BACKGROUND TO THE INVENTION

The field of recombinant antibody technology has rapidly progressed during the last two decades, mainly because of the interest in their human therapeutic use. The ability to select specific human antibodies by display technologies and to improve their affinity, stability, and expression level by molecular evolution has further boosted the field. Whole antibodies are complex molecules that consist of heavy and light chains. Although isolated antibody heavy and light chains can retain antigen-binding specificity, their affinity and solubility is often reduced. However, the paired N-terminal variable domains of heavy (VH) and light (VL) chains are sufficient for antigen binding. Such antibody fragments can be produced as monovalent antibody fragment (Fab) or as single-chain Fv (scFv) where the VH and VL domains are joined by a polypeptide linker. The serendipitous discovery that camelids produce functional antibodies devoid of light chains (Hamers-Casterman et al (1993) *Nature* 363:446-448)) formed a new way of thinking in the field because it was subsequently shown that their single N-terminal domain (VHH, also referred to as Nanobody®) binds antigen without requiring domain pairing. These heavy-chain only antibodies also lack the CH1 domain, which in a conventional antibody associates with the light chain and to a lesser degree interacts with the VH domain. Such single-domain antibodies were later also identified in particular cartilaginous fish (Greenberg et al (1995) *Nature* 374:168-173) and together with the VHHs are often designated as immunoglobulin single variable domain antibodies (ISVD). ISVDs present interesting therapeutic possibilities owing to their small size, high stability, ease of modification by genetic fusions and good production levels in microorganisms. When Nanobodies® are produced in eukaryotic cells about a tenth of them is glycosylated (see Functional Glycomics, Jun. 11, 2009). However, glycosylation is generally avoided for the production of ISVDs in eukaryotic hosts and hence glycosylation acceptor sites are mutated as the presence of a glycan can introduce heterogeneity, or interfere with folding and antigen recognition. The small size of ISVDs can also be a therapeutic disadvantage because of their rapid clearance from circulation when administered to patients. On the other hand, the small size of ISVDs offers opportunities for coupling ISVDs to half-life extension molecules, or coupling to specific drugs (e.g. formation of antibody-drug conjugates) or tracers. A variety of coupling methods are described in the art (e.g. especially applied in the field of the modification of monoclonal antibodies) and these technologies focus for example on conjugation via primary amine groups (lysine residues and N-terminus) or via cysteines, by acylation or alkylation, respectively. However, site-control of conjugation is generally low and full homogeneity is seldom obtained. Glycan-specific conjugation of monoclonal antibodies offers more homogeneity as described by Synaffix BV (see for example WO2014065661, WO2015057065 and WO2015057064) but this strategy suffers from the fact that the native glycans are used and the chemical coupling methods are expensive. Application WO2018206734 discloses specific sites in ISVDs which can be efficiently glycosylated. In one aspect it would be desirable to identify additional sites in ISVDs which can be modified with glycan structures which do not encumber the binding or folding functions of ISVDs and which would lead to an efficient glycosylation and result in homogeneous, ready-to-use-for-chemical-coupling glycan structures when produced in a suitable production system. Importantly, specific glycosylation sites on ISVDs cannot be chosen in an arbitrary matter since the efficiency of glycosylation of introduced glycosylation sites is unpredictable and needs to be evaluated on an individual basis.

SUMMARY OF THE INVENTION

An important object of the present application is to provide polypeptides comprising immunoglobulin variable domains (IVDs), wherein the IVDs have one or more glycosylation acceptor sites present in specifically selected regions which have been identified via a rational design approach. The presence of these one or more glycosylation acceptor sites at specific regions in an IVD allows for efficient glycosylation without encumbering the binding affinities of the IVDs with their ligand and without interfering with the folding of the IVDs. Importantly, IVDs can be recombinantly produced in suitable host cells comprising homogenous forms of glycans at specific positions which can be further modified with a variety of moieties as herein explained further.

Thus, according to a first aspect, the following is provided: a nucleotide sequence encoding a polypeptide comprising an immunoglobulin variable domain (IVD), wherein the IVD comprises an amino acid sequence that comprises 4 framework regions (FR) and 3 complementarity determining regions (CDR) according to the following formula (1): FR1-CDR1-FR2-CDR2-FR3-CDR3-FR4 (1), wherein said IVD has at least one glycosylation acceptor site present at an amino acid selected from positions 50 and/or 52 and/or 97 and/or 99 of the IVD (according to AHo numbering convention).

In a particular aspect said IVD is an immunoglobulin single variable domain. The glycosylation acceptor site of the IVD can be an asparagine residue that can be N-glycosylated. Particularly, the glycosylation acceptor site of said IVD contains an NXT, NXS, NXC or NXV motif (wherein X can be any amino acid except proline (P)) such that the asparagine residue of the NXT/NXS/NXC/NXV motif is present at any of positions 50 and/or 52 and/or 97 and/or 99 of the IVD (according to AHo numbering convention). In specific embodiments the IVD has an additional glycosylation acceptor site in the IVD, such as position 14 and/or 48 and/or 103 (according to AHo numbering convention).

In another aspect, a polypeptide comprising an IVD is provided, which is encoded by a nucleotide sequence of the invention.

According to other aspects expression vectors comprising said nucleotide sequence and a cell comprising the expression vector are provided.

A recombinant cell is, according to particular embodiments, a higher eukaryotic cell, such as a mammalian cell or a plant cell, a lower eukaryotic cell, such as a filamentous fungus cell or a yeast cell, or in certain conditions also a prokaryotic cell. Of particular relevance are glyco-engineered cells, particularly glyco-engineered lower eukaryotic cells.

More particularly, the higher eukaryotic cells according to the invention are vertebrate cells, in particular mammalian cells. Examples include, but are not limited to, CHO cells or HEK293 cells (e.g. HEK293S cells).

Using these cells IVDs can be produced which are modified with glycans at specific rationally chosen sites. Glycoengineered cells are of particular advantage as they are favorable for the production of IVDs modified with particularly desired glycans and/or homogeneous glycans. This homogenous glycosylation profile is highly desirable as a product is obtained whose properties are well predictable.

Moreover, the above described cells are useful for the production of IVDs which are directly in the cell modified with GlcNAc, LacNAc, or Sialyl-LacNAc glycans being favorable for conjugation. Moreover, employment of these cells leads to IVDs with homogenous glycosylation profiles. Thus, particular benefits over conventional approaches are achieved as the obtained products are highly homogenous. This is in contrast with conventional approaches which typically require in vitro enzymatic treatment of heterogeneous glycans to provide GlcNAc, Gal, or Sia residues as starting points for further modification. Besides high costs, in vitro enzymatic treatment might risk incomplete processing and thus a heterogeneous product. Another conventional approach is based on direct processing of heterogeneously glycosylated proteins and accordingly, the resulting products again lack homogeneity.

According to specific aspects, the polypeptide according to the invention comprises an IVD, which is glycosylated. The glycosylation can, according to specific embodiments, comprise one or more glycans with a terminal GlcNAc, GalNAc, Galactose, Sialic Acid, Glucose, Glucosamine, Galactosamine, Bacillosamine, Mannose or Mannose-6-P sugar or a chemically modified monosaccharide such as GalNAz, GlcNAz, or azido-Sialic acid present in one or more glycans.

According to other specific embodiments, the glycosylation consists of one or more glycans selected from the list consisting of GlcNAc, LacNAc (=GlcNAc-Gal), sialyl-LacNAc, Man5GlcNAc2, Man8GlcNAc2, Man9GlcNAc2, Man10GlcNAc2, complex glycans, hybrid glycans and GlcNAz, GlcNAc-GalNAz, and LacNAc-Azido-Sialic acid (see Alan D. McNaught (1996) *Pure & Appl. Chem.* Vol. 68, No 10, 1919-2008 for Nomenclature of Carbohydrates). IVDs modified at certain positions with the above described glycans are particularly useful for glycan-specific conjugation. Especially a glycosylation profile consisting of GlcNAc, LacNAc, or sialyl-LacNAc is of advantage for site-specific conjugation.

In specific aspects, an IVD conjugate is provided comprising a polypeptide according to the invention and a conjugated moiety, which is conjugated to the glycan.

IVDs modified with glycans at rationally chosen positions are an ideal starting point for glycan-based conjugation. Linkage of a moiety to a glycan present on an IVD for example allows for the production of IVD conjugates, wherein the ratio of IVD and conjugated moiety is well-defined.

Even more advantageous are IVDs modified with homogenous glycans allowing for particularly efficient conjugation. Conjugation can be performed either chemically (e.g. using periodate oxidation of the glycan component and subsequent conjugation via methods known in the art such as oxime ligation, hydrazone ligation, or via reductive amination) or enzymatically (e.g. using Galactose Oxidase to oxidize Galactose and subsequent conjugation via oxime ligation, hydrazone ligation, or via reductive amination). Alternatively, tagged glycan residues may be incorporated to allow subsequent conjugation reactions (e.g. incorporation of GalNAz in the glycan chain using a mutant galactosyltransferase, and subsequent conjugation reaction via click chemistry).

The conjugated moiety can comprise a half-life extending moiety, a therapeutic agent, a detection unit or a targeting moiety. The opportunities to use the glycans on IVDs according to the invention as a bio-orthogonal handle for conjugation to drugs, tracers, and the like via glycan conjugation methodologies are not limited to the examples described herein.

In other aspects the invention provides a polypeptide comprising an IVD according to the previous aspects wherein the glycosylation of said polypeptide consists of one or more glycans selected from the group consisting of GlcNAc, LacNAc, sialyl-LacNAc, Man5GlcNAc2, Man8GlcNAc2, Man9GlcNAc2, Man10GlcNAc2, hypermannosylated glycans, mannose-6-phosphate glycans, complex glycans and hybrid glycans.

In still other aspects the invention provides a polypeptide as described herein for use as a medicament.

In other aspects the invention provides a polypeptide comprising an IVD according to the previous aspects wherein the glycosylation of said polypeptide consists of one or more glycans selected from the group consisting of GlcNAc, LacNAc, sialyl-LacNAc, Man5GlcNAc2, Man8GlcNAc2, Man9GlcNAc2, Man10GlcNAc2, hypermannosylated glycans, mannose-6-phosphate glycans, complex glycans and hybrid glycans for use to prevent and/or treat gastrointestinal diseases.

In an other aspect the polypeptides are used for oral delivery to the gastrointestinal tract.

In other aspects the invention provides an IVD conjugate comprising a polypeptide as described herein, and a conjugated moiety such as a half-life extending moiety, a therapeutic agent, a detection unit or a targeting moiety which conjugated moiety is connected to an N-linked glycan.

In other aspects the invention provides a pharmaceutical composition comprising a polypeptide as described herein or an IVD conjugate as described herein.

FIGURE LEGENDS

FIGS. 1A and 1B: in silico analysis of the GBP nanobody. FIG. 1A. Crystal structure of the GBP nanobody in complex with the GFP antigen (from PDB entry 3ogo). CDR regions are depicted in orange. FIG. 1B. Starting from the 3ogo GBP crystal structure, 4 N-linked glycosylation sequons were introduced at previously identified sites (Q14N-P15A-G16T, G27N-P30T, P48N-K50T, and R86N (according to AHo numbering system)) and $Man_{10}GlcNAc_2$ N-glycans were appended to their respective Asn residues. Subsequently, the space occupancy of the glycans was investigated via molecular dynamics to explore which additional regions of the nanobody could accommodate an N-glycan without interfering with target binding and which spatially complement the previously identified N-glycosylation sites.

FIG. 2: Secondary structure topology of the GFP-binding nanobody GBP. Specific sites selected for introduction of N-linked glycosylation signatures in the GBP nanobody are depicted (numbering in the figure refers to the aHo numbering scheme). Black dots represent previously identified sites for efficient N-glycosylation (see WO2018206734); the grey dots represent the new sites.

FIG. 3: Coomassie Blue stained SDS-PAGE gel analysis of the different 'glycovariants' of GBP, expressed in the *Pichia pastoris* GlycoSwitchM5 (GSM5) strain. Mutations performed to yield a specific variant are indicated (according to the AHo numbering scheme); Gins and GGins indicate insertion of 1 or 2 glycine residues, respectively; numbers indicate the different clones that were tested for each variant.

FIG. 4: Melting curves of GBP glycovariants. Upper and lower pane represent 2 separate sets of experiments. The upper pane shows melting curves for the previously identified preferred variants; the lower pane shows melting curves for the newly identified preferred variants; variant P48N-K50T (C-terminal His6-tag) was included in both experiment sets. Data points represent mean values of triplicate experiments, standard deviations are indicated by shading.

FIG. 5: Parameters for GFP binding kinetics of GBP glycovariants as determined by biolayer interferometry. Left and right pane represent 2 separate sets of experiments. The left pane shows the data for the previously identified preferred variants; the right pane shows the data for the newly identified preferred variants; variant P48N-K50T(His6) was included in both experiment sets.

FIG. 6: $Man_9GlcNAc_2$ glycans at positions 14, 27, 48, 86 and 99 rarely occupy the space near the CDRs of GBP. Molecular dynamics simulation of GBP (cyan, CDR in orange) carrying $Man_9GlcNAc_2$ glycans (green) at five engineered N-glycosylation sites (variant M1: Q14N-P15A-G16T, G27N-P30T, P48N-K50T, R86N, and E99N). The trajectories followed by the glycans during the MD run (1000 ns) are delineated using isomeshes (iso-contour level 0.005; N14 glycan—marine blue; N27 glycan—firebrick red; N48 glycan—forest green; N86 glycan—orange; N99 glycan—hotpink).

FIG. 7: $Man_9GlcNAc_2$ glycans at positions 14, 27, 48, 86 and 97 rarely occupy the space near the CDRs of GBP. Molecular dynamics simulation of GBP (cyan, CDR in orange) carrying $Man_9GlcNAc_2$ glycans (green) at five engineered N-glycosylation sites (variant M2: Q14N-P15A-G16T, G27N-P30T, P48N-K50T, R86N, and K97N-P98A-E99T). The trajectories followed by the glycans during the MD run (1000 ns) are delineated using isomeshes (iso-contour level 0.005; N14 glycan—marine blue; N27 glycan—firebrick red; N48 glycan—forest green; N86 glycan—orange; N97 glycan—pink).

FIG. 8: Man9GlcNAc2 glycans at positions 14, 27, 50, 86 and 99 rarely occupy the space near the CDRs of GBP. Molecular dynamics simulation of GBP (cyan, CDR in orange) carrying $Man_9GlcNAc_2$ glycans (green) at five engineered N-glycosylation sites (variant M3: Q14N-P15A-G16T, G27N-P30T, K50N-R52T, R86N, and E99N). The trajectories followed by the glycans during the MD run (1000 ns) are delineated using isomeshes (iso-contour level 0.005; N14 glycan—marine blue; N27 glycan—firebrick red; N50 glycan—splitpea green; N86 glycan—orange; N99 glycan—hotpink).

FIG. 9: $Man_9GlcNAc_2$ glycans at positions 14, 27, 50, 86 and 97 rarely occupy the space near the CDRs of GBP. Molecular dynamics simulation of GBP (cyan, CDR in orange) carrying $Man_9GlcNAc_2$ glycans (green) at five engineered N-glycosylation sites (variant M4: Q14N-P15A-G16T, G27N-P30T, K50N-R52T, R86N, and K97N-P98A-E99T). The trajectories followed by the glycans during the MD run (1000 ns) are delineated using isomeshes (iso-contour level 0.005; N14 glycan—marine blue; N27 glycan—firebrick red; N50 glycan—splitpea green; N86 glycan—orange; N97 glycan—pink).

BRIEF DESCRIPTION OF THE FIGURES

The patent or application file contains at least one drawing executed in color. Copies of this patent or patent application publication with color drawing(s) will be provided by the Office upon request and payment of the necessary fee.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Figure 1A:
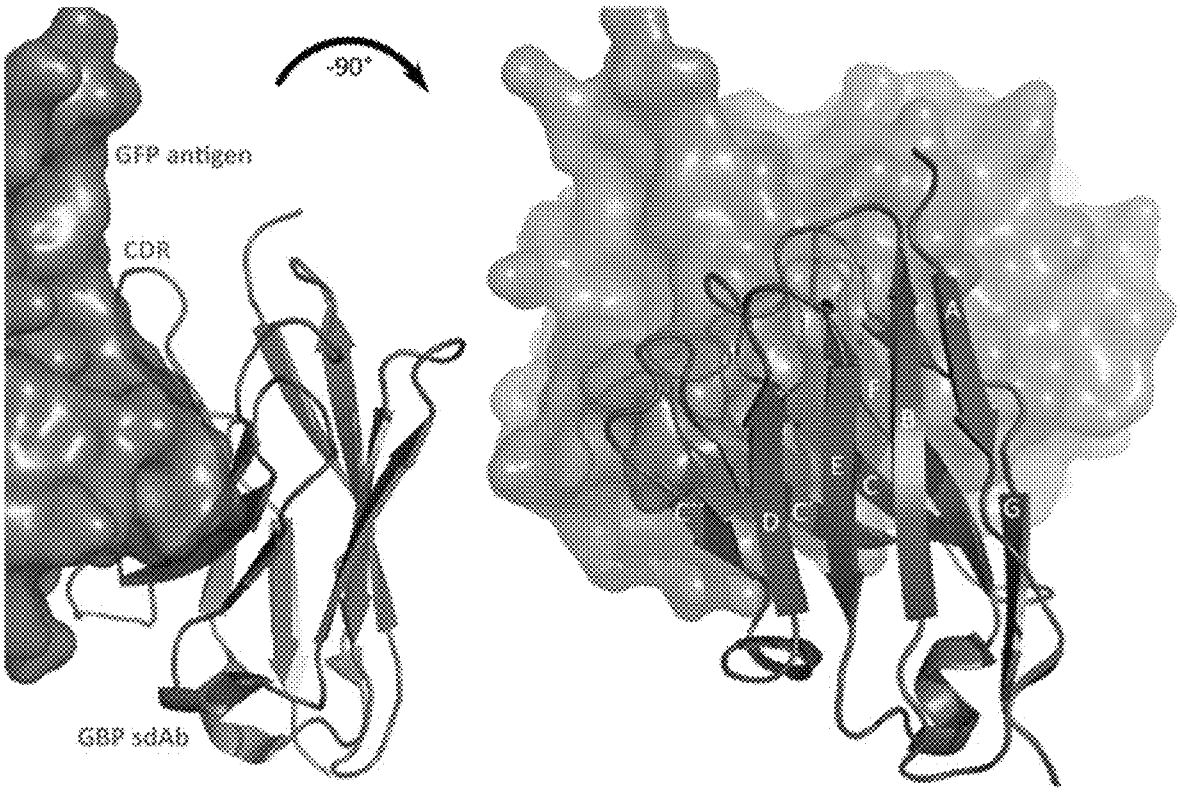

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, New York (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

As used herein, the term "nucleotide sequence" refers to a polymeric form of nucleotides of any length, either deoxyribonucleotides or ribonucleotides, or analogs thereof. Nucleotide sequences may have any three-dimensional structure, and may perform any function, known or unknown. Non-limiting examples of nucleotide sequences include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleotide sequence may be linear or circular.

As used herein, the term "polypeptide" refers to a polymeric form of amino acids of any length, which can include coded and non-coded amino acids, chemically or biochemically modified or derivatized amino acids, and polypeptides having modified peptide backbones. Polypeptide sequences can be depicted with the single-letter (or one letter) amino acid code or the three-letter amino acid code as depicted here below:

| Amino acid | Three letter code | One letter code |
|---|---|---|
| alanine | ala | A |
| arginine | arg | R |
| asparagine | asn | N |
| aspartic acid | asp | D |
| asparagine of aspartic acid | asx | B |
| cysteine | cys | C |
| glutamic acid | glu | E |
| glutamine | gln | Q |
| glutamine or glutamic acid | glx | Z |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The term "immunoglobulin single variable domain" (abbreviated as "ISVD"), equivalent to the term "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associated) immunoglobulin domains such as light and heavy chain variable domains, i.e., by a VH-VL pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs.

As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody.

For example, the immunoglobulin single variable domain may be a (single) domain antibody (or an amino acid sequence that is suitable for use as a (single) domain antibody), a "dAb" or dAb (or an amino acid sequence that is suitable for use as a dAb) or a Nanobody (as defined herein, and including but not limited to a VHH); other single variable domains, or any suitable fragment of any one thereof.

In particular, the immunoglobulin single variable domain may be a Nanobody® (as defined herein) or a suitable fragment thereof. [Note: Nanobody®, Nanobodies® and Nanoclone® are registered trademarks of Ablynx N.V.] For a general description of Nanobodies, reference is made to the further description below, as well as to the prior art cited herein, such as e.g. described in WO 08/020079 (page 16).

"VHH domains", also known as VHHs, $V_H$H domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al (1993) *Nature* 363: 446-448). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "VL domains" or "VL domains"). For a further description of VHHs and Nanobodies, reference is made to the review article by Muyldermans (*Reviews in Molecular Biotechnology* 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164. For a further general description of Nanobodies, reference is made to the prior art cited herein, such as e.g., described in WO 08/020079 (page 16).

"Domain antibodies", also known as "Dabs", "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans.

It should also be noted that single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g., described in Davies and Riechmann (*FEBS* 339: 285-290, 1994; *Biotechnol.* 13: 475-479, 1995; *Prot. Eng.* 9: 531-537, 1996) and Riechmann and Muyldermans (*J. Immunol. Methods* 231: 25-38, 1999).

For numbering of the amino acid residues of an IVD different numbering schemes can be applied. For example, numbering can be performed according to the AHo numbering scheme for all heavy (VH) and light chain variable domains (VL) given by Honegger, A. and Plückthun, A. (*J. Mol. Biol.* 309, 2001), as applied to VHH domains from camelids. Alternative methods for numbering the amino acid residues of VH domains, which can also be applied in an analogous manner to VHH domains, are known in the art. For example, the delineation of the FR and CDR sequences can be done by using the Kabat numbering system as applied to VHH domains from camelids in the article of Riechmann, L. and Muyldermans, S., 231(1-2), *J Immunol Methods*. 1999. Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113. In the present description, examples and claims, the numbering according to AHo as described above will be followed.

It should be noted that—as is well known in the art for VH domains and for VHH domains—the total number of amino acid residues in each of the CDRs may vary and may not correspond to the total number of amino acid residues indicated by the Kabat numbering or AHo numbering (that is, one or more positions according to the Kabat numbering or AHo may not be occupied in the actual sequence, or the actual sequence may contain more amino acid residues than the number allowed for by the Kabat numbering or AHo numbering). This means that, generally, the numbering according to Kabat or AHo may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Immunoglobulin single variable domains such as Domain antibodies and Nanobodies (including VHH domains) can be subjected to humanization. In particular, humanized immunoglobulin single variable domains, such as Nanobodies (including VHH domains) may be immunoglobulin single variable domains that are as generally defined for in the previous paragraphs, but in which at least one amino acid residue is present (and in particular, at least one framework residue) that is and/or that corresponds to a humanizing substitution (as defined herein). Potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on what is described before, (the framework regions of) an immunoglobulin single variable domain, such as a Nanobody (including VHH domains) may be partially humanized or fully humanized.

Immunoglobulin single variable domains such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (*Biotechnology* 10:779-783, 1992), Barbas, et al. (*Proc. Nat. Acad. Sci, USA* 91: 3809-3813, 1994), Shier et al. (*Gene* 169: 147-155, 1995), Yelton et al. (*Immunol.* 155: 1994-2004, 1995), Jackson et al. (*J. Immunol.* 154: 3310-9, 1995), Hawkins et al. (*J. Mol. Biol.* 226: 889 896, 1992), Johnson and Hawkins (Affinity maturation of antibodies using phage display, Oxford University Press, 1996).

The process of designing/selecting and/or preparing a polypeptide, starting from an immunoglobulin single variable domain such as a Domain antibody or a Nanobody, is also referred to herein as “formatting” said immunoglobulin single variable domain; and an immunoglobulin single variable domain that is made part of a polypeptide is said to be “formatted” or to be “in the format of” said polypeptide. Examples of ways in which an immunoglobulin single variable domain can be formatted and examples of such formats will be clear to the skilled person based on the disclosure herein; and such formatted immunoglobulin single variable domain form a further aspect of the invention.

The term “Glycosylation acceptor site” refers to a position within the IVD, which can be N- or O-glycosylated. N-linked glycans are typically attached to asparagine (Asn), while O-linked glycans are commonly linked to the hydroxyl oxygen of serine, threonine, tyrosine, hydroxylysine, or hydroxyproline side-chains.

An “NXT”, “NXS”, “NXC” or “NXV” motif refers to the consensus sequences Asn-Xaa-Thr/Ser or Asn-Xaa-Cys/Val, wherein Xaa can be any amino acid except proline (Shrimal, S. and Gilmore, R., *J Cell Sci.* 126(23), 2013, Sun, S. and Zhang, H., *Anal. Chem.* 87 (24), 2015). It is well known in the art that potential N-glycosylation acceptor sites are specific to the consensus sequence Asn-Xaa-Thr/Ser or Asn-Xaa-Cys/Val. It has been shown in the art that the presence of proline between Asn and Thr/Ser leads to inefficient N-glycosylation. In a particular aspect, the N-linked glycosylation acceptor site of an IVD or ISVD according to the invention is expanded with aromatic residues like natural or engineered aromatic amino acid residues such as Phenylalanine (F), Tyrosine (Y), Histidine (H) or Tryptophane (VV). Such modifications are described i.e. in Price, J. L. et al., *Biopolymers.* 98(3), 2012 and in Murray, A. N. et al., *Chem Biol.* 22(8), 2015. In a more particular embodiment, the aromatic residues are located at position −1 (F/Y/H/W-N-x-T/S), −2 (F/Y/H/W-x1-N-x-T/S), or −3 (F/Y/H/W-x2-x1-N-x-T/S) relative to the Asparagine (N) residue in the N-linked glycosylation sequon (N-x-T/N-x-S) (Murray A N et al (2015) *Chem. Biol.* 22(8):1052-62) and Price J L et al (2012) Biopolymers 98(3):195-211). In addition, it is also known that proline (P) residues immediately upstream or downstream of the N-x-T sequon can negatively impact glycosylation efficiency (Bañó-Polo, M. et al. (2011) Protein *Science* 20, 179-186; Mellquist, J. L. et al. (1998) *Biochemistry* 37, 6833-6837), therefore it can be beneficial to generate variants with ‘extended’ glycosylation sequons (GG-N-x-T, G-N-x-T, N-x-T-G, N-x-T-GG); in these variants, one or more glycine (G) residues are introduced introduced immediately upstream/downstream of the N-x-T sequon to avoid vicinal prolines. All these described modifications are particularly useful to increase glycosylation efficiency of an N-glycosylation acceptor site, glycan homogeneity, and glycoprotein stability.

The term “expression vector”, as used herein, includes any vector known to the skilled person, including plasmid vectors, cosmid vectors, phage vectors, such as lambda phage, viral vectors, such as adenoviral, AAV or baculoviral vectors, or artificial chromosome vectors such as bacterial artificial chromosomes (BAC), yeast artificial chromosomes (YAC), or P1 artificial chromosomes (PAC). Expression vectors generally contain a desired coding sequence and appropriate promoter sequences necessary for the expression of the operably linked coding sequence in a particular host organism (e.g. higher eukaryotes, lower eukaryotes, prokaryotes). Typically, a vector comprises a nucleotide sequence in which an expressible promoter or regulatory nucleotide sequence is operatively linked to, or associated with, a nucleotide sequence or DNA region that codes for an mRNA, such that the regulatory nucleotide sequence is able to regulate transcription or expression of the associated nucleotide sequence. Typically, a regulatory nucleotide sequence or promoter of the vector is not operatively linked to the associated nucleotide sequence as found in nature, hence is heterologous to the coding sequence of the DNA region operably linked to. The term “operatively” or “operably” “linked” as used herein refers to a functional linkage between the expressible promoter sequence and the DNA region or gene of interest, such that the promoter sequence is able to initiate transcription of the gene of interest, and refers to a functional linkage between the gene of interest and the transcription terminating sequence to assure adequate termination of transcription in eukaryotic cells. An “inducible promoter” refers to a promoter that can be switched ‘on’ or ‘off’ (thereby regulating gene transcription) in response to external stimuli such as, but not limited to, temperature, pH, certain nutrients, specific cellular signals, et cetera. It is used to distinguish between a “constitutive promoter”, by which a promoter is meant that is continuously switched ‘on’, i.e. from which gene transcription is constitutively active.

A “glycan” as used herein generally refers to glycosidically linked monosaccharides, oligosaccharides and polysaccharides. Hence, carbohydrate portions of a glycoconjugate, such as a glycoprotein, glycolipid, or a proteoglycan are referred to herein as a "glycan". Glycans can be homo- or heteropolymers of monosaccharide residues, and can be linear or branched. N-linked glycans may be composed of GalNAc, Galactose, neuraminic acid, N-acetylglucosamine, Fucose, Mannose, and other monosaccharides, as also exemplified further herein.

In eukaryotes, O-linked glycans are assembled one sugar at a time on a serine or threonine residue of a peptide chain in the Golgi apparatus. Unlike N-linked glycans, there are no known consensus sequences but the position of a proline residue at either −1 or +3 relative to the serine or threonine is favourable for O-linked glycosylation.

"Complex N-glycans" as used in the application refers to structures with typically one, two or more (e.g. up to six) outer branches, most often linked to an inner core structure Man3GlcNAc2. The term "complex N-glycans" is well known to the skilled person and defined in literature. For instance, a complex N-glycan may have at least one branch, or at least two, of alternating GlcNAc and optionally also Galactose (Gal) residues that may terminate in a variety of oligosaccharides but typically will not terminate with a Mannose residue. For the sake of clarity a single GlcNAc, LacNAc, sialyl-LacNAc or an azide-modified version of these present on an N-glycosylation site of a glycoprotein (thus lacking the inner core structure Man3GlcNAc2) is not regarded as a complex N-glycan.

"Hypermannosyl glycans" are N-glycans comprising more than 10 mannose residues. Typically such hypermannosyl glycans are produced in lower eukaryotic cells such as yeast cells, specifically wild type yeast cells such as wild type *Pichia pastoris*. N-glycans produced in yeast cells such as *Pichia pastoris* can also be mannose-6-phosphate modified.

A "higher eukaryotic cell" as used herein refers to eukaryotic cells that are not cells from unicellular organisms. In other words, a higher eukaryotic cell is a cell from (or derived from, in case of cell cultures) a multicellular eukaryote such as a human cell line or another mammalian cell line (e.g. a CHO cell line). Typically, the higher eukaryotic cells will not be fungal cells. Particularly, the term generally refers to mammalian cells, human cell lines and insect cell lines. More particularly, the term refers to vertebrate cells, even more particularly to mammalian cells or human cells. The higher eukaryotic cells as described herein will typically be part of a cell culture (e.g. a cell line, such as a HEK or CHO cell line), although this is not always strictly required (e.g. in case of plant cells, the plant itself can be used to produce a recombinant protein).

By "lower eukaryotic cell" a filamentous fungus cell or a yeast cell is meant. Yeast cells can be from the species *Saccharomyces* (e.g. *Saccharomyces cerevisiae*), *Hansenula* (e.g. *Hansenula polymorpha*), *Arxula* (e.g. *Arxula adeninivorans*), *Yarrowia* (e.g. *Yarrowia lipolytica*), *Kluyveromyces* (e.g. *Kluyveromyces lactis*), or *Komagataella phaffii* (Kurtzman, C. P. (2009) *J Ind Microbiol Biotechnol.* 36(11) which was previously named and better known under the old nomenclature as *Pichia pastoris* and also further used herein. According to a specific embodiment, the lower eukaryotic cells are *Pichia* cells, and in a most particular embodiment *Pichia pastoris* cells. In specific embodiments the filamentous fungus cell is *Myceliopthora thermophila* (also known as C1 by the company Dyadic), *Aspergillus* species (e.g. *Aspergillus nidulans, Aspergillus niger, Aspergillus oryzae, Aspergillus japonicus*), *Fusarium* species (e.g. *Fusarium venenatum*), Hypocrea and *Trichoderma* species (e.g. *Trichoderma reesei*).

"Prokaryotic cells" typically refer to non-pathogenic prokaryotes like bacterial cells such as for example *E. coli, Lactococcus* and *Bacillus* species.

According to a particular embodiment, the cell of the present invention is a glyco-engineered cell. A "glyco-engineered cell" refers to a cell that has been genetically modified so that it expresses proteins with an altered N-glycan structure and/or O-glycan structure as compared to in a wild type background. Typically, the naturally occurring modifications on glycoproteins have been altered by genetic engineering of enzymes involved in the glycosylation pathway. In general, sugar chains in N-linked glycosylation may be divided in three types: high-mannose (typically yeast), complex (typically mammalian) and hybrid type glycosylation. Besides that, a variety of O-glycan patterns exist, for example with yeast oligomannosylglycans differing from mucin-type O-glycosylation in mammalian cells. The different types of N- and O-glycosylation are all well known to the skilled person and defined in the literature. Considerable effort has been directed towards the identification and optimization of strategies for the engineering of eukaryotic cells that produce glycoproteins having a desired N- and/or O-glycosylation pattern and are known in the art (e.g. De Pourcq, K. et al., Appl Microbiol Biotechnol. 87(5), 2010). One non-limiting example of such a glyco-engineered expression system is described in patent application WO2010015722 and relates to a (higher or lower) eukaryotic cell expressing both an endoglucosaminidase and a target protein, and wherein the recombinant secreted target proteins are characterized by a uniform N-glycosylation pattern (in particular one single GlcNAc residue (in lower eukaryotes) or a modification thereof such as GlcNAc modified with Galactose (LacNAc) or sialyl-LacNAc (in mammalian cells). Also encompassed are cells genetically modified so that they express proteins or glycoproteins in which the glycosylation pattern is human-like or humanized (i.e. complex-type glycoproteins). This can be achieved by providing cells, in particular lower eukaryotic cells, having inactivated endogenous glycosylation enzymes and/or comprising at least one other exogenous nucleic acid sequence encoding at least one enzyme needed for complex glycosylation. Endogenous glycosylation enzymes which could be inactivated include the alpha-1,6-mannosyltransferase Och1p, Alg3p, alpha-1,3-mannosyltransferase of the Mnn1p family, beta-1,2-mannosyltransferases. Enzymes needed for complex glycosylation include, but are not limited to: N-acetylglucosaminyl transferase I, N-acetylglucosaminyl transferase II, mannosidase II, galactosyltransferase, fucosyltransferase and sialyltransferase, and enzymes that are involved in donor sugar nucleotide synthesis or transport. Still other glyco-engineered cells, in particular yeast cells, that are envisaged here are characterized in that at least one enzyme involved in the production of high mannose structures (high mannose-type glycans) is not expressed. Enzymes involved in the production of high mannose structures typically are mannosyltransferases. In particular, alpha-1,6-mannosyltransferases Och1p, Alg3p, alpha-1,3-mannosyltransferase of the Mnn1p family, beta-1,2-mannosyltransferases may not be expressed. Thus, a cell can additionally or alternatively be engineered to express one or more enzymes or enzyme activities, which enable the production of particular N-glycan structures at a high yield. Such an enzyme can be targeted to a host subcellular organelle in which the enzyme will have optimal activity, for example, by means of signal peptide not normally associated with the enzyme. It should be clear that the enzymes described herein and their activities are well-known in the art.

Also envisaged herein as “glyco-engineered cells” according to the invention are cells as described in WO2010015722 and WO2015032899 (further designated herein as GlycoDelete cells, or cells having a GlycoDelete background). In brief, such a cell is engineered to reduce glycosylation heterogeneity and at least comprises a nucleotide sequence encoding an endoglucosaminidase enzyme and an expression vector comprising a nucleotide sequence encoding a target polypeptide.

As heterogeneity in glycosylation does not only originate from N-linked sugars, but also from 0-glycans attached to the glycoprotein, it can be desirable to remove these diverse carbohydrate chains from the polypeptides of the invention. This can be achieved by expressing an endoglucosaminidase enzyme in a cell that is deficient in expression and/or activity of an endogenous UDP-Galactose 4-epimerase (GalE) as described in WO2017005925. Cells described in the latter application are also envisaged as glyco-engineered cells according to the present invention and herein further described as GlycoDoubleDelete cells or cells having a GlycoDoubleDelete background.

Also particularly referred to herein as “glyco-engineered cells” are non-mammalian cells engineered to mimic the human N-glycosylation pathway (i.e. GlycoSwitch®, see also Laukens, B. et al (2015) *Methods Mol Biol.* 1321 and Jacobs, P. P. et al. (2009) *Nat Protoc.* 4(1)).

An “IVD conjugate” or an “ISVD conjugate” is referred to herein as a polypeptide comprising an IVD or ISVD of the invention which is coupled (or conjugated or connected, which are equivalent terms in the art) with a specific moiety, herein further defined as the “conjugated moiety”. Coupling between the IVD conjugate or ISVD conjugate can occur via a specific amino acid (e.g. lysine, cysteine) present in the IVD or ISVD. Preferably coupling occurs via the at least one introduced glycan (e.g. an introduced N-glycan) present in the polypeptide sequence of said IVD or ISVD. Glycan-specific conjugation can be performed with glycans present in an introduced glycan site of the IVD or ISVD. In specific cases glycans can be modified further in vitro (e.g. trimmed with specific exoglycosidase enzymes) before they are coupled to a “conjugated moiety”. In addition, coupling can also occur as a combination between i) a specific amino acid present in said IVD or ISVD and a conjugated moiety and ii) the coupling via the introduced glycan and a conjugated moiety. Conjugation may be performed by any method described in the art and some non-limiting illustrative embodiments are outlined herein below.

As used herein, the term “conjugated moiety” comprises agents (e.g. proteins (e.g. a second IVD or ISVD), nucleotide sequences, lipids, (other) carbohydrates, polymers, peptides, drug moieties (e.g. cytotoxic drugs), tracers and detection agents) with a particular biological or specific functional activity. For example, an IVD or ISVD conjugate comprising a polypeptide according to the invention and a conjugated moiety has at least one additional function or property as compared to the unconjugated IVD or ISVD polypeptide of the invention. For example, an IVD or ISVD conjugate comprising a polypeptide of the invention and a cytotoxic drug being the conjugated moiety results in the formation of a binding polypeptide with drug cytotoxicity as second function (i.e. in addition to antigen binding conferred by the IVD or ISVD polypeptide). In yet another example, the conjugation of a second binding polypeptide to the IVD or ISVD polypeptide of the invention may confer additional binding properties. In certain embodiments, where the conjugated moiety is a genetically encoded therapeutic or diagnostic protein or nucleotide sequence, the conjugated moiety may be synthesized or expressed by either peptide synthesis or recombinant DNA methods that are well known in the art. In another aspect, where the conjugated moiety is a non-genetically encoded peptide, e.g. a drug moiety, the conjugated moiety may be synthesized artificially or purified from a natural source.

The present invention aims to provide polypeptides comprising IVDs or ISVDs having at least one glycosylation acceptor site present in specific regions, in particular in regions allowing for efficient glycosylation and which glycosylation does not interfere with the binding and folding of the IVDs or ISVDs, that makes them more amenable for further use, e.g. production of IVD or ISVD conjugates.

In yet another embodiment the invention provides a nucleotide sequence encoding a polypeptide comprising an immunoglobulin variable domain (IVD), wherein the IVD comprises an amino acid sequence that comprises 4 framework regions (FR) and 3 complementarity determining regions (CDR) according to the following formula (1): FR1-CDR1-FR2-CDR2-FR3-CDR3-FR4 (1), wherein said IVD has at least one glycosylation acceptor site present at an amino acid selected from positions 50 and/or 52 and/or 97 and/or 99 of the IVD (according to AHo numbering convention).

In a specific embodiment the immunoglobulin variable domain (IVD) is an immunoglobulin single variable domain (ISVD).

In yet another specific embodiment the at least one glycosylation acceptor site of said IVD or ISVD is an asparagine residue that can be N-glycosylated.

In yet another specific embodiment the IVD or ISVD contains an NXT, NXS, NXC or NXV motif (in which X can be any amino acid) such that the asparagine residue of the NXT/NXS/NXC/NXV motif is present at an amino acid selected from positions 50 and/or 52 and/or 97 and/or 99 of the IVD (according to AHo numbering convention).

In yet another embodiment the invention provides a nucleotide sequence encoding a polypeptide comprising an immunoglobulin variable domain (IVD), wherein the IVD comprises an amino acid sequence that comprises 4 framework regions (FR) and 3 complementarity determining regions (CDR) according to the following formula (1): FR1-CDR1-FR2-CDR2-FR3-CDR3-FR4 (1), wherein said IVD has at least one glycosylation acceptor site present at an amino acid selected from positions 50 and/or 52 and/or 97 and/or 99 of the IVD (according to AHo numbering convention) and wherein said IVD has at least one additional glycosylation acceptor site, selected from the amino acid range 83 to 88 and/or at an amino acid selected from the amino acid range 27 to 40 and/or amino acid position 14 and/or 48 and/or 103 (according to AHo numbering convention).

Said glycosylation acceptor site can be modified (but not necessarily) with an N- or an O-linked glycan. For example, a glycosylation acceptor site for N-linked glycans is the amino acid asparagine. It is particularly envisaged herein that the invention is not limited to N-glycosylation. The present disclosure provides means to employ both N- and O-glycosylation.

The wording ‘selected from the amino acid range 83 to 88’ means that the glycosylation acceptor site can be present an any of amino acids 83, 84, 85, 86, 87 or 88 (according to AHo numbering convention).

In yet another embodiment the IVD of the invention has, according to particular embodiments, still can have an at least one additional glycosylation acceptor site present at position 16 and/or 49 and/or 139.

Thus, it is clear that the scope of the present invention includes the simultaneous use of at least two or even more glycosylation acceptor sites within the IVD of the present invention. Based on the present application, the skilled person knows how to select additional glycosylation acceptor sites within or next to the specific glycosylation acceptor sites identified in the IVDs of the invention and identification/or use of further positions and their combination is also within the scope of the invention as presented.

According to a particular embodiment, a nucleotide sequence encoding a polypeptide comprising an ISVD as described before is provided, wherein said ISVD is a heavy chain variable domain sequence. According to a more particular embodiment, the ISVD is a heavy chain variable domain sequence that is derived from a heavy chain antibody, preferably a camelid heavy chain antibody.

In another particular embodiment, a nucleotide sequence encoding a polypeptide comprising an ISVD as described before is provided, wherein said polypeptide consists of said ISVD.

In yet another embodiment an expression vector is provided comprising a nucleotide sequence encoding a polypeptide comprising an IVD as described before.

In the present invention the term 'comprising a polypeptide comprising an ISVD' means that an ISVD can be fused (or coupled) to another polypeptide such as a half-life extending polypeptide (e.g. a VHH directed to serum albumin), a second VHH (such as to create a bispecific or bivalent IgG), an enzyme, a therapeutic protein, an Fc domain such as an IgA Fc domain or an IgG Fc domain.

In yet another embodiment the invention provides a cell comprising an expression vector according to the invention. In particular embodiments, the cell is a higher eukaryotic cell, such as a mammalian cell or a plant cell, a lower eukaryotic cell, such as a filamentous fungus cell or a yeast cell, or a prokaryotic cell.

Higher eukaryotic cells can be of any higher eukaryotic organism, but in particular embodiments mammalian cells are envisaged. The nature of the cells used will typically depend on the desired glycosylation properties and/or the ease and cost of producing the IVD or ISVD described herein. Mammalian cells may for instance be used to avoid problems with immunogenicity. Higher eukaryotic cell lines for protein production are well known in the art, including cell lines with modified glycosylation pathways. Non-limiting examples of animal or mammalian host cells suitable for harboring, expressing, and producing proteins for subsequent isolation and/or purification include Chinese hamster ovary cells (CHO), such as CHO-K1 (ATCC CCL-61), DG44 (Chasin et al., 1986, Som. Cell Molec. Genet., 12:555-556; and Kolkekar et al., 1997, Biochemistry, 36:10901-10909), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), dihydrofolate reductase negative CHO cells (CHO/-DHFR, Urlaub and Chasin, 1980, Proc. Natl. Acad. Sci. USA, 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293T cells, or 293 cells subcloned for growth in suspension culture, Graham et al., 1977, J. Gen. Virol., 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, Biol. Reprod., 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, Annals NYAcad. Sci., 383:44-68); MCR 5 cells; FS4 cells. According to particular embodiments, the cells are mammalian cells selected from CHO cells, Hek293 cells or COS cells. According to further particular embodiments, the mammalian cells are selected from CHO cells and Hek293 cells.

According to other particular embodiments, the cell according to the invention is a plant cell. Typical plant cells comprise cells from tobacco, tomato, carrot, maize, algae, alfalfa, rice, soybean, *Arabidopsis thaliana, Taxus cuspidata, Nicotiana benthamiana*, and *Catharanthus roseus*. Still additional plant species which can be useful for the production of IVD or ISVD polypeptides according to the invention are described in Weathers, P. J. et al., *Appl Microbiol Biotechnol.* 85(5), 2010.

In more particular embodiments, the cell according to the invention is a lower eukaryotic cell, such as a filamentous fungus cell or a yeast cell. Specific examples of filamentous fungi and yeast cells have been outlined herein before.

In more particular embodiments, the cell according to the invention is a prokaryotic cell, such as *E. coli, Lactococcus* species or *Bacillus* species.

In more particular embodiments, the cell according to the invention as described before is a glyco-engineered cell. A glyco-engineered cell can be capable of removing unwanted N-glycosylation and/or O-glycosylation. The term glyco-engineered cell has been outlined herein before. A glyco-engineered cell can also be a non-mammalian cell engineered to mimic the human glycosylation pathway as described before.

In a particular embodiment, a polypeptide comprising an IVD encoded by a nucleotide sequence according to the invention as described before is provided, wherein the polypeptide comprises at least one glycan wherein the glycan has a terminal GlcNAc, GalNAc, galactose, sialic acid, glucose, glucosamine, galactosamine, bacillosamine (a rare amino sugar (2,4-diacetamido-2,4,6-trideoxyglucose) described for example in *Bacillus subtilus* and *Campylobacter jejuni*), Mannose or Mannose-6-P sugar or a chemically modified monosaccharide such as GalNAz, Azidosialic acid (AzSia), or GlcNAz. IVD polypeptides comprising a glycan with the specific sugars can be made in vivo. For example higher eukaryotic cells will typically generate glycans with terminal sialic acid, yeast cells will typically generate glycans with terminal mannose or mannose-6P, certain filamentous fungus will generate glycans with a terminal galactose, certain glycoengineered yeast cells produce terminal GlcNAc (e.g. described in WO2010015722), certain glycoengineered higher eukaryotic cells produce mixtures of glycans with terminal GlcNAc, galactose and sialic acid (e.g. described in WO2010015722 and WO2015032899), other glycoengineered higher eukaryotic cells produce glycans with terminal GlcNAc (see WO2017005925), eukaryotic cells comprising certain mutant galactosyltransferases can enzymatically attach GalNAc to a non-reducing GlcNAc sugar (see WO2004063344), eukaryotic cells comprising mutant galactosyltransferase which are fed with UDP-GalNAz (a C2-substituted azidoacetamido-galactose UDP-derivative) will incorporate GalNAz at a terminal non-reducing GlcNAc of a glycan (see WO2007095506 and WO2008029281). Optionally IVD polypeptides comprising a glycan with the specific sugars can be made by a combination of in vivo followed by in vitro trimming of the glycan until the desired terminal sugar is obtained, e.g. WO2015057065 (Synaffix).

In yet another particular embodiment the invention provides a polypeptide comprising an IVD of the present invention wherein the IVD comprises at least one glycan and wherein the glycan consists of a glycan selected from the group consisting of GlcNAc, LacNAc, sialyl-LacNAc, Man5GlcNAc2, Man8GlcNAc2, Man9GlcNAc2, Man10GlcNAc2, hyper-mannosylated glycans, mannose-6-phosphate glycans, complex glycans, hybrid glycans and chemically modified glycans such as GlcNAz, GlcNAc-GalNAz, azido-sialic acid-LacNAc.

In yet another particular embodiment the invention provides a composition comprising a polypeptide comprising an IVD of the present invention wherein the IVD comprises at least one glycan and wherein the glycan consists of a glycan selected from the group consisting of GlcNAc, LacNAc, sialyl-LacNAc, Man5GlcNAc2, Man8GlcNAc2, Man9GlcNAc2, Man10GlcNAc2, hypermannosyl glycans, mannose-6-phosphate glycans, complex glycans, hybrid glycans and chemically modified glycans such as GlcNAz, GlcNAc-GalNAz, azido-sialic acid-LacNAc, wherein the relative amount (e.g. calculated in molecular weight) of one or more of these glycans at a particular position or positions in said polypeptide is at least 20%, at least 30%, at least 40%, at least 50%, at least 60%, at least 70%, at least 80% or at least 90% with respect to the same polypeptide in the sample.

While the variety of host cells described herein before can be particularly useful to produce specific glycans present on the IVDs provided by the invention, it should be kept in mind that also combined in vivo and in vitro approaches are possible to obtain the desired glycan structure. Indeed, IVDs or ISVDs of the invention which have been produced in eukaryotic hosts can be purified, the glycan structures can be trimmed by suitable endoglucosaminidases or exoglycosidases and thereafter can be re-built by the in vitro use of a variety of glycosyltransferases (e.g. galactosyltransferases, sialyltransferases, polysialyltransferases and the like).

IVD (and ISVD)-Conjugates

In a particular embodiment the invention provides IVD (and ISVD)-conjugates. In a preferred embodiment the IVD or ISVD polypeptides according to the invention are coupled to a specific moiety (a conjugated moiety as defined herein before) via the one or more glycan structures present on said IVD or ISVD polypeptides. Such glycan specific coupling to a specific moiety is referred to in the art as glycan-specific conjugation. Glycan structures with specific terminal carbohydrates or specific glycan structures as herein described before present on the IVD or ISVD polypeptides are used as a starting point for the coupling with a specific moiety.

Specific Moieties which can be Used for Conjugation

A number of moieties are described in the art which can be used for coupling to the at least one glycan structure present in the IVD or ISVD of the invention. Conjugated moieties comprise for example a half-life extending moiety, a therapeutic agent, a detection unit, a targeting moiety or even a second (the same or different) IVD or ISVD polypeptide. One or more conjugated moieties, which can also be different from each other, can be linked to the IVD or ISVD of the invention. Even one conjugated moiety can have more than one function, i.e. a half-life extending moiety can at the same time be useful as a targeting moiety. The present invention specifically incorporates the part of the description teaching specific moieties in WO2018206734 (starting on page 27, line 28 to page 30, line 8).

Linkers Useful in the IVD (and ISVD)-Conjugates

In certain embodiments the IVD (or ISVD)-conjugates comprise a linker between the glycan and the targeting moiety. Certain linkers are more useful than others and the use of a specific linker will depend on the application. The present invention specifically incorporates the part of the description teaching specific linkers in WO2018206734 (starting on page 30, line 9 to page 31, line 30).

In yet another embodiment the invention provides a method to produce a polypeptide comprising an IVD of the invention, said method comprises the steps of introducing an expression vector comprising a nucleotide sequence encoding an IVD of the invention in a suitable expression host, expressing and isolating said IVD of the invention. Suitable conditions have to be chosen to express the polypeptide comprising an IVD according to the invention.

By the term "a suitable cell" a higher eukaryotic cell, such as a mammalian cell or a plant cell, a lower eukaryotic cell, such as a filamentous fungus cell or a yeast cell which is optionally glyco-engineered, is envisaged as explained above.

Particularly envisaged herein is the production of polypeptides comprising an IVD or IVSD according to the invention, wherein said polypeptide is glycosylated and comprises one or more glycans.

For example, a polypeptide comprising an IVD of the invention, wherein the polypeptide is N-glycosylated and comprises a mixture of N-glycans with a terminal GlcNAc, Galactose or Sialic Acid can typically be obtained by expression in a higher eukaryotic glyco-engineered cell according to the invention as described in WO2010015722 and WO2015032899. For example a polypeptide comprising an IVD of the invention, wherein the polypeptide is N-glycosylated and comprises or essentially comprises an N-glycan with a terminal GlcNAc can be produced in a lower eukaryotic cell as described in WO2010015722. For example an N-glycan with a terminal GlcNAc can be produced in a glyco-engineered cell deficient in expression and/or activity of an endogenous UDP-Galactose 4-epimerase (GalE) as described in WO2017005925.

Also particularly envisaged herein is the production of polypeptides comprising an IVD according to the invention, wherein the glycosylation of said polypeptide consists of one or more glycans selected from the group consisting of GlcNAc, LacNAc, sialyl-LacNAc, Man5GlcNAc2, Man8GlcNAc2, Man9GlcNAc2, Man10GlcNAc2, complex glycans, hybrid glycans and GlcNAc-GalNAz. Even more particularly envisaged herein is the production of polypeptides comprising an IVD according to the invention, wherein the glycosylation of said polypeptide consists of one or more glycans selected from the group consisting of GlcNAc, LacNAc, sialyl-LacNAc, Man5GlcNAc2, Man8GlcNAc2, Man9GlcNAc2, Man10GlcNAc2 and complex glycans.

A polypeptide comprising an IVD of the invention, wherein the polypeptide is glycosylated and wherein the glycosylation consists of GlcNAc, LacNAc and sialyl-LacNAc glycans is typically obtained in a glyco-engineered mammalian cell according to the invention as described in WO2010015722 and WO2015032899, although such GlcNAc, LacNAc and sialyl-LacNAc glycans could also be engineered in lower eukaryotic cells (e.g. via the introduction of the mammalian complex glycosylation pathway in yeast). A polypeptide comprising an IVD of the invention, wherein the polypeptide is glycosylated and wherein the glycosylation consists of a GlcNAc can be produced in a glyco-engineered cell according to the invention, which can be deficient in expression and/or activity of an endogenous UDP-Galactose 4-epimerase (GalE) as described in WO2017005925. A polypeptide comprising an IVD of the invention, wherein the polypeptide is glycosylated and wherein the glycosylation consists of a complex glycan can be produced in a higher eukaryotic cell according to the invention, which is optionally glyco-engineered. A polypeptide comprising an IVD of the invention, wherein the polypeptide is glycosylated and wherein the glycosylation consists of one or more glycans selected from the group consisting of Man5GlcNAc2 glycans, Man8GlcNAc2 glycans, Man9GlcNAc2 glycans, hypermannosylated glycans, mannose-6-phosphate modified glycans and complex glycans can be produced in glyco-engineered cells according to the invention, particularly in yeast cells.

Coupling Methods to Link Specific Moieties to an IVD

In yet another embodiment the invention provides methods to produce an IVD or ISVD conjugate of the invention. Generally, such methods start by introducing an expression vector comprising a nucleotide sequence encoding an IVD according to the invention in a suitable cell of choice, followed by expressing the IVD polypeptide for some time, purifying the IVD polypeptide and linking of a specific conjugated moiety to the purified IVD polypeptide. The coupling method itself is generally carried out in vitro.

Several possibilities exist in the art to link a specific conjugated moiety an IVD polypeptide of the invention. Generally spoken there are chemical, enzymatic and combined chemo-enzymatic conjugation strategies to carry out the coupling reaction. The present invention specifically incorporates the part of the description teaching specific moieties in WO2018206734 (starting on page 33, line 10 to page 35, line 5).

Applications of IVDs and IVD-Conjugates of the Invention

In a particular embodiment, a polypeptide comprising an IVD-conjugate of the invention is used to modulate the circulation half-life or to increase the IVD stability, for selective targeting, to modulate immunogenicity of the IVD-conjugate or for detection purposes.

In yet another embodiment the IVD-conjugates of the invention are used as a medicament.

In yet another embodiment the IVD (not conjugated with any moiety) of the invention is used as a medicament.

In yet another embodiment the invention provides a glycosylated polypeptide comprising an immunoglobulin variable domain (IVD), wherein the IVD comprises an amino acid sequence that comprises 4 framework regions (FR) and 3 complementarity determining regions (CDR) according to the following formula (1): FR1-CDR1-FR2-CDR2-FR3-CDR3-FR4 (1), wherein said IVD has at least one glycosylation acceptor site present at an amino acid selected from positions 50 and/or 52 and/or 97 and/or 99 of the IVD (according to AHo numbering convention).

In yet another embodiment the invention provides a glycosylated polypeptide comprising an immunoglobulin variable domain (IVD), wherein the IVD comprises an amino acid sequence that comprises 4 framework regions (FR) and 3 complementarity determining regions (CDR) according to the following formula (1): FR1-CDR1-FR2-CDR2-FR3-CDR3-FR4 (1), wherein said IVD has at least one glycosylation acceptor site present at an amino acid selected from positions 50 and/or 52 and/or 97 and/or 99 of the IVD (according to AHo numbering convention) and wherein the IVD has at least one additional glycosylation acceptor selected from the amino acid range 83 to 88 and/or at an amino acid selected from the amino acid range 27 to 40 and/or amino acid position 14 and/or 48 and/or 103 (according to AHo numbering convention).

In yet another embodiment the invention provides a glycosylated IVD as herein described in the previous embodiments for use as a medicament.

It is understood that the IVD molecules, the nucleotide acid sequences encoding the IVD molecules, the glycosylated IVD molecules, pharmaceutical compositions comprising IVD molecules, pharmaceutical compositions comprising glycosylated IVD molecules, glycosylated IVD molecules which are conjugates with a moiety, pharmaceutical compositions comprising IVD molecules coupled to conjugated moieties can be used for human as well for veterinary applications.

In yet another embodiment the IVD (not conjugated with any moiety) of the invention is used to prevent pre-antibody binding.

In yet another embodiment the IVD (not conjugated with any moiety) of the invention is used to reduce immunogenicity.

With the wording "to modulate circulation half-life" it is meant that the half-life of the polypeptide (e.g. IVD-conjugate) can be either increased or decreased. For some applications, it can be useful that the polypeptide comprising an IVD of the invention or IVD-conjugate of the invention remains in the bloodstream for a shorter time than polypeptides or conjugates lacking the specific properties of polypeptides or IVD-conjugates as claimed. Often, prolonged half-life is aimed as many therapeutic molecules are smaller than the renal filtration threshold and are rapidly lost from the circulation thereby limiting their therapeutic potential. As a non-limiting example, albumin or other half-life extending moieties as referred to above can be used in a variety of ways known to the skilled practitioner to increase the circulatory half-life of such molecules.

With "selective targeting" it is meant that polypeptides and IVD-conjugates of the invention can be useful to achieve an exclusive effect on the target of interest. An example of this is conventional chemotherapy where selective targeting of cancer cells without interacting with the normal body cells often fails. As a consequence thereof serious side effects are caused including organ damage resulting in impaired treatment with lower dose and ultimately low survival rates. Polypeptides and IVD-conjugates of the invention, optionally comprising a targeting moiety, can be useful to overcome the disadvantages of conventional approaches not limited to cancer therapy.

Using polypeptides and conjugates of the invention to modulate the immunogenicity can be achieved when compared to polypeptides or IVD-conjugates lacking the specific properties of polypeptides or IVD-conjugates as claimed. For example, for long-term treatment preference is given to low immunogenicity. Particularly and non-limiting, the glycans as described herein can be utilized as a tool to modify immunogenicity. The skilled person can adapt immunogenicity based on common knowledge and the disclosure provided herein.

The polypeptides and conjugates as described herein can be used to prevent or reduce binding to pre-existing antibodies. This effect has been described in literature for glycans on an ISVD (see i.e. WO2016150845). Use of polypeptides and conjugates according to the invention to prevent pre-antibody binding is within the scope of the present disclosure and envisaged herein.

Polypeptides and conjugates of the invention are also provided for detection purposes, particularly when comprising a detection unit as explained before. Particularly, polypeptides and conjugates of the invention are more prone for detection purposes than polypeptides or conjugates lacking the specific properties of the claimed polypeptides or conjugates.

Thus, in a particular embodiment the IVD-conjugates of the invention can also be used for diagnostic purposes.

In yet another embodiment the invention provides kits comprising IVDs of the present invention.

In yet another embodiment the invention provides kits comprising IVD-conjugates of the present invention.

In another embodiment, a pharmaceutical composition is provided comprising a polypeptide comprising an IVD or an IVD-conjugate as described before.

Therefore, the present invention includes pharmaceutical compositions that are comprised of a pharmaceutically acceptable carrier and a pharmaceutically effective amount of polypeptides, nucleotide sequences and IVD-conjugates of the invention and a pharmaceutically acceptable carrier. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of polypeptides, nucleotide sequences and conjugates of the invention and a pharmaceutically acceptable carrier is preferably that amount which produces a result or exerts an influence on the particular condition being treated. The polypeptides, nucleotide sequences and conjugates of the invention and a pharmaceutically acceptable carrier can be administered with pharmaceutically acceptable carriers well known in the art using any effective conventional dosage form, including immediate, slow and time-release preparations, and can be administered by any suitable route such as any of those commonly known to those of ordinary skill in the art. For therapy, the pharmaceutical composition of the invention can be administered to any patient in accordance with standard techniques. The administration can be by any appropriate mode, including orally, parenterally, topically, nasally, ophthalmically, intrathecally, intracerebroventricularly, sublingually, rectally, vaginally, and the like. Still other techniques of formulation as nanotechnology and aerosol and inhalant are also within the scope of this invention. The dosage and frequency of administration will depend on the age, sex and condition of the patient, concurrent administration of other drugs, counter-indications and other parameters to be taken into account by the clinician.

The pharmaceutical composition of this invention can be lyophilized for storage and reconstituted in a suitable carrier prior to use.

When prepared as lyophilization or liquid, physiologically acceptable carrier, excipient, stabilizer need to be added into the pharmaceutical composition of the invention (Remington's Pharmaceutical Sciences 22th edition, Ed. Allen, Loyd V, Jr. (2012). The dosage and concentration of the carrier, excipient and stabilizer should be safe to the subject (human, mice and other mammals), including buffers such as phosphate, citrate, and other organic acid; antioxidant such as vitamin C, small polypeptide, protein such as serum albumin, gelatin or immunoglobulin; hydrophilic polymer such as PVP, amino acid such as amino acetate, glutamate, asparagine, arginine, lysine; glycose, disaccharide, and other carbohydrate such as glucose, mannose or dextrin, chelate agent such as EDTA, sugar alcohols such as mannitol, sorbitol; counterions such as Na+, and/or surfactant such as TWEEN™, PLURONICS™ or PEG and the like.

The preparation containing pharmaceutical composition of this invention should be sterilized before injection. This procedure can be done using sterile filtration membranes before or after lyophilization and reconstitution.

The pharmaceutical composition is usually filled in a container with sterile access port, such as an i.v. solution bottle with a cork. The cork can be penetrated by hypodermic needle.

It is to be understood that although particular embodiments, specific configurations as well as materials and/or molecules, have been discussed herein for nucleotide sequences, cells, polypeptides, conjugates and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

1. Use of Molecular Dynamics Simulations to Map the Glycans on Glyco-Engineered ISVDs We recently used a rational design approach for the targeted introduction of N-linked glycans into the scaffold of ISVDs (see WO2018206734). We started from the available crystallographic structure of a representative immunoglobulin single variable domain polypeptide. In our rational design approach, we reasoned that potential regions in the secondary structure for the introduction of an N-glycan should not interfere with (or should not disrupt) the antigen recognition site of the antibody and, importantly, should not hamper the formation of beta sheets during the folding. As the CDR regions of a nanobody are important for antigen recognition and the beta-sheet structure is important for the correct folding, the hypothesis was made that protein regions between the CDR regions and beta strands would probably be less sensitive to minor modifications such as the attachment of N-glycans.

In an experimental setup, multiple preferred sites were identified that can be glycosylated with a high efficiency (high site occupancy), and this without compromising fold stability or target recognition. We also showed that multiple N-glycosylation sites can be successfully engineered in one nanobody scaffold.

In this invention, we aim to identify novel glycosylation-compatible sites that can spatially complement the previously identified N-glycosylation sites (see WO2018206734) and further expand the ISVD glycosylation landscape. A GFP-binding nanobody (abbreviated as GBP and published by Kubala, M. H. et al (2010) Protein Sci. 19(12)) was selected as the benchmark ISVD.

The amino acid sequence of the nanobody GBP is depicted in SEQ ID NO: 1.
In SEQ ID NO: 1 the CDR1, CDR2 and CDR3 regions are underlined. SEQ ID NO: 2 depicts CDR1, SEQ ID NO: 3 depicts CDR2, SEQ ID NO: 4 depicts CDR3, SEQ ID NO: 5 depicts FR1, SEQ ID NO: 6 depicts FR2, SEQ ID NO: 7 depicts FR3 and SEQ ID NO: 8 depicts FR4.

SEQ ID NO: 1:
QVQLVESGGALVQPGGSLRLSCAASGFPVNRYSMRWYRQAPGKEREWVAGM

SSAGDRSSYEDSVKGRFTISRDDARNTVYLQMNSLKPEDTAVYYCNVNVGF

EYWGQGTQVTVSSHHHHHH (121 amino acids)

SEQ ID NO: 2 (CDR1):
GFPVNRYS

SEQ ID NO: 3 (CDR2):
MSSAGDRSS

SEQ ID NO: 4 (CDR3):
NVNVGFE

SEQ ID NO: 5 (FR1):
QVQLVESGGALVQPGGSLRLSCAAS

SEQ ID NO: 6 (FR2):
MRWYRQAPGKEREWAG

SEQ ID NO: 7 (FR3):
YEDSVKGRFTISRDDARNTVYLQMNSLKPEDTAVYYC

SEQ ID NO: 8 (FR4):
YWGQGTQVTVSS

Figure 1B:
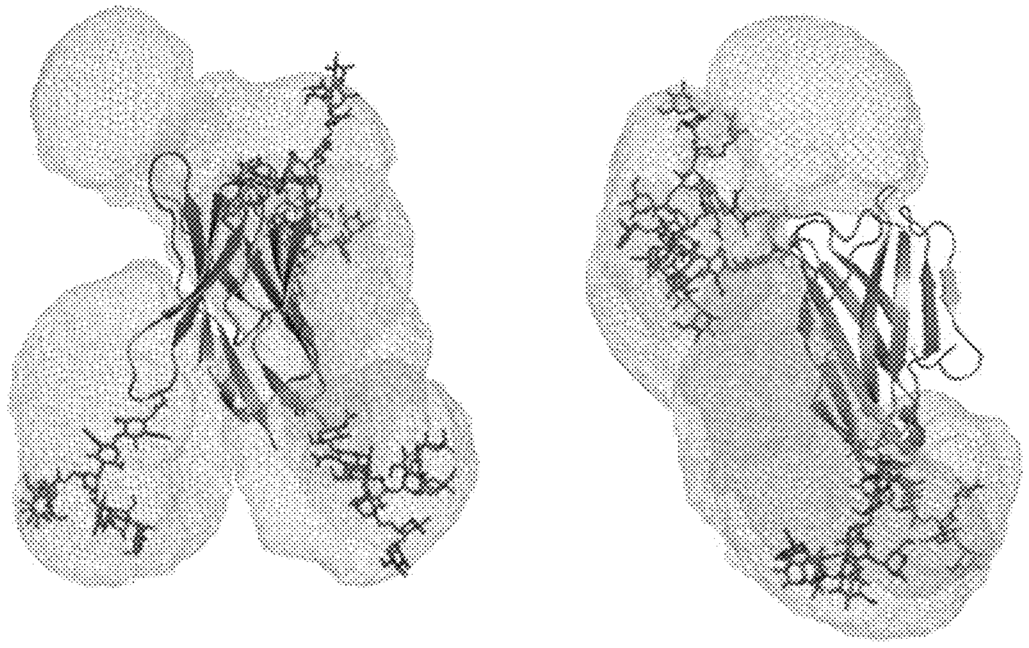

Starting from the 3ogo GBP crystal structure, we introduced 4 N-linked glycosylation sequons at the previously (see WO2018206734) identified preferred sites (Q14N-P15A-G16T, G27N-P30T, P48N-K50T, and R86N (according to AHo numbering system)) and appended $Man_{10}GlcNAc_2$ N-glycans to their respective Asn residues. Subsequently, we investigated the space occupancy of the glycans via molecular dynamics simulations. The simulations revealed that the glycans introduced at sites 14, 27, 48, and 86 steer clear of the CDRs, but also that these glycans cluster to one side of the nanobody. Using the simulation data as a guide, we were able to identify additional loop regions which could accommodate an N-glycan without interfering with target binding and which could spatially complement the previously identified N-glycosylation sites (see FIGS. 1A and 1B).

Figure 2:
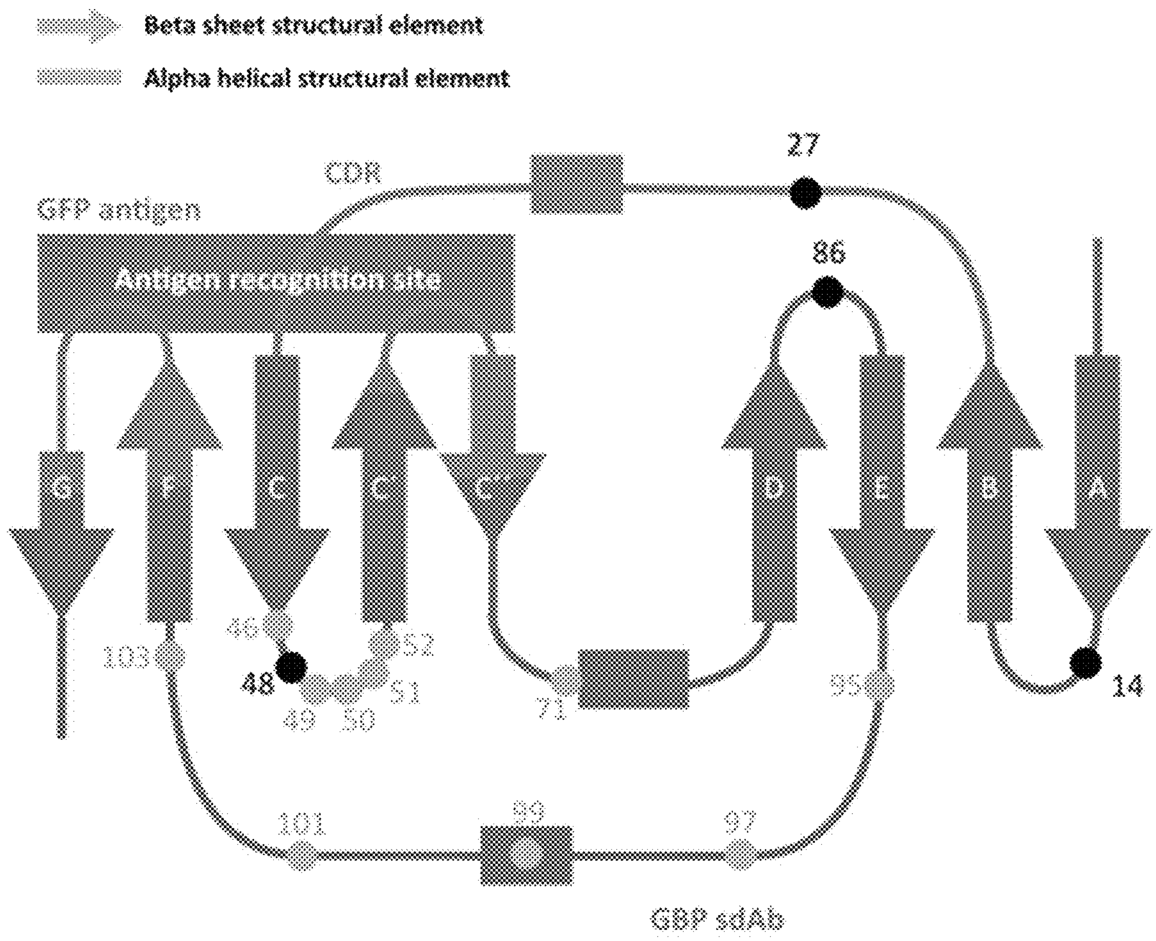

2. Selection of Regions/Sites in the ISVD Scaffold for the Introduction of Additional N-Glycosylation Signatures To spatially complement the previously identified preferred N-glycosylation sites, in WO2018206734, with additional sites, we used the crystal structure and the molecular dynamics data as a guide to select 3 regions for the introduction of additional artificial glycosylation sites. Based on the criteria outlined in example 1, we selected specific amino acid sequences within the 3 selected protein regions of nanobody GBP for the introduction of N-x-T N-linked glycosylation sequons, and envisioned introduction of N-linked glycans at positions 46, 49, 50, 51, 52, 71, 95, 97, 99, 101, and 103 (AHo numbering; see FIG. 2).

3. Experimental Validation of the Selected N-Glycosylation Sites

Figure 3:
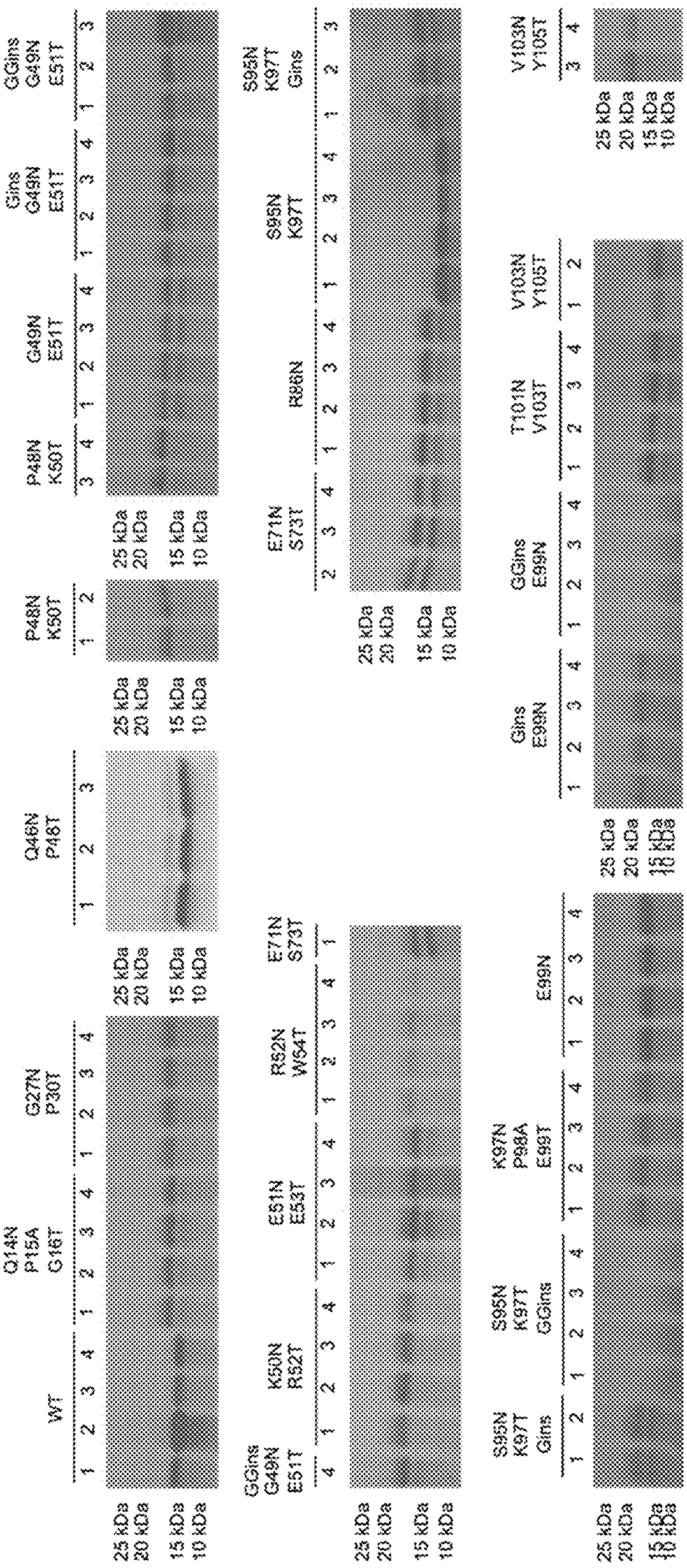

The rationally designed and proposed N-glycosylation acceptor sites specified in Example 2 were introduced into the GBP nanobody. As it has been reported that proline (P) residues immediately upstream or downstream of the N-x-T sequon can negatively impact glycosylation efficiency (Bañó-Polo, M. et al. (2011) *Protein Science* 20, 179-186; Mellquist, J. L. et al. (1998) *Biochemistry* 37, 6833-6837), we also generated some variants with 'extended' glycosylation sequons (GG-N-x-T, G-N-x-T, N-x-T-G, N-x-T-GG); in these variants, glycine (G) residues were introduced immediately upstream/downstream of the N-x-T sequon to avoid vicinal prolines. GBP variants with an N-x-T sequon at the previously identified sites 14, 27, 48, and 86 (AHo numbering) were included as reference controls. All the GBP variants were equipped with a C-terminal histidine-tag (8×HIS) which facilitates purification and/or detection. The specific mutations introduced to obtain N-glycan acceptor sites in nanobody GBP are given in Table 1. The coding sequences of the wild type GBP nanobody and the different mutants with introduced N-glycosylation acceptor sites in specific positions as given in Table 1 were operably linked to the AOX1 promoter (a methanol inducible promoter) of *Pichia pastoris*. The resulting expression vectors were introduced in the GlycoSwitch M5 (GSM5) strain of *Pichia pastoris*, which modifies its glycoproteins with predominantly $Man_5GlcNAc_2$ structures (Jacobs, P. P. et al., (2009) *Nat Protoc.* 4(1)). The different recombinant *Pichia pastoris* cultures were then first grown in medium containing glycerol as the sole carbon source for 48 h at 28° C., and subsequently recombinant protein expression was induced by substitution of glycerol for methanol. After another 48 hours at 28° C., the growth medium (supernatant) was collected of each recombinant culture. The culture supernatants were assayed via Coomassie Blue stained SDS-PAGE. Results of this analysis are shown in FIG. 3.

Our data show that glycosylation of nanobody GBP could be obtained for almost all the glycovariants we designed (except for the S95N-K97T, S95N-K97T-GGins and the GGins-E99N variants (aHo numbering)) albeit with varying efficiency of N-glycosylation. In some cases (Gins-G49N-E51T and GGins-G49N-E51T versus G49N-E51T; S95N-K97T-Gins versus S95N-K97T), insertion of glycine residues between a chosen N-x-T site and a vicinal proline residue positively impacted glycosylation efficiency. An overview of the glycosylation efficiency based on (visual) band density on Coomassie Brilliant Blue-stained SDS-PAGE is depicted in Table 1. The glyco-engineered nanobodies containing the previously identified sites 14, 27, 48, and 86 (see WO2018206734) were glycosylated with a high site occupancy. Remarkably, 5 additional positions were identified that also allow highly efficient glycosylation of the nanobody protein structure: position 50, position 52, position 97, position 99, and position 103. Also remarkably, four of these positions (50, 52, 97 and 99) have never been described for nanobodies with respect to introduction of N-glycan sites. Positions 103 has been cited accidently in WO2016150845. Of note is that the N glycosylation site introduced at site 99 displayed an exceptionally high site occupancy despite the presence of a vicinal proline. Positions 14, 27, 48, 86, 50, 52, 97, 99, and 103 are according to the AHo numbering.

TABLE 1

| Overview of the GBP N-glycosylation variants. | | | | | | | |
|---|---|---|---|---|---|---|---|
| Vector | Insert | Modification (AHo) | Pichia strain | N-glyc. type | N-glyc. efficiency | Validation | Location |
| ppExpr | GBP | WT(ref) | GSM5 | — | — | CB | — |
| ppExpr | GBP | Q14N-P15A-G16T (ref) | GSM5 | Man5 | ++ | CB | Loop A-B |
| ppExpr | GBP | G27N-P30T (ref) | GSM5 | Man5 | +++ | CB | Loop B-C |
| ppExpr | GBP | Q46N-P48T | GSM5 | Man5 | + | CB | Loop C-C' |
| ppExpr | GBP | P48N-K50T (ref) | GSM5 | Man5 | ++ | CB | Loop C-C' |
| ppExpr | GBP | G49N-E51T | GSM5 | Man5 | + | CB | Loop C-C' |
| ppExpr | GBP | Gins-G49N-E51T | GSM5 | Man5 | ++ | CB | Loop C-C' |
| ppExpr | GBP | GGins-G49N-E51T | GSM5 | Man5 | ++ | CB | Loop C-C' |
| ppExpr | GBP | K50N-R52T | GSM5 | Man5 | +++ | CB | Loop C-C' |
| ppExpr | GBP | E51N-E53T | GSM5 | Man5 | ++ | CB | Loop C-C' |
| ppExpr | GBP | R52N-W54T | GSM5 | Man5 | +++ | CB | Loop C-C' |
| ppExpr | GBP | E71N-S73T | GSM5 | Man5 | + | CB | Loop C''-D |
| ppExpr | GBP | R86N (ref) | GSM5 | Man5 | ++ | CB | Loop D-E |
| ppExpr | GBP | S95N-K97T | GSM5 | Man5 | - | CB | Loop E-F |
| ppExpr | GBP | S95N-K97T-Gins | GSM5 | Man5 | + | CB | Loop E-F |
| ppExpr | GBP | S95N-K97T-GGins | GSM5 | Man5 | Not expressed | CB | Loop E-F |
| ppExpr | GBP | K97N-P98A-E99T | GSM5 | Man5 | +++ | CB | Loop E-F |
| ppExpr | GBP | E99N | GSM5 | Man5 | +++ | CB | Loop E-F |
| ppExpr | GBP | Gins-E99N | GSM5 | Man5 | +++ | CB | Loop E-F |
| ppExpr | GBP | GGins-E99N | GSM5 | Man5 | Not expressed | CB | Loop E-F |
| ppExpr | GBP | T101N-V103T | GSM5 | Man5 | ++ | CB | Loop E-F |
| ppExpr | GBP | V103N-Y105T | GSM5 | Man5 | +++ | CB | Loop E-F |

Pichia strain GSM5 = GlycoSwitchM5 (alternative name for the Pichia Kai3 strain). N-glycosylation type Man5 = $Man_5GlcNAc_2$. CB = Coomassie Brilliant Blue stained SDS-PAGE analysis. N-glycosylation efficiency: — (no glycosylation), +, ++, +++ (from low to high site occupancy), Not expressed (glycovariant could not be detected in the medium of transformed cells).

To assess the site occupancy of N-linked glycans, GBP and glyco-engineered GBP variants with a glycan at position 14, 27, 46, 48, 50, 86, 97, and 99 were heat-denatured in buffer containing 5% SDS and 400 mM DTT and treated with *H. jecorina* endoT (Stals I. et al (2010) *FEMS Microbiology Letters,* 303(1), 9-17). After the endoT digest, all samples were characterized by intact protein mass spectrometry. LC-MS was performed on an Ultimate 3000 HPLC (Thermo Fisher Scientific, Bremen, Germany) equipped with a Poroshell 300SB-C8 column (Thermo Scientific 1.0 mm of I.D.×150 mm), in-line connected with an ESI source to a LTQ XL mass spectrometer (Thermo Fischer Scientific). Mobile phases were 0.1% formic acid and 0.05% trifluoroacetic acid (TFA) in $H_2O$ (solvent A) and 0.1% formic acid and 0.05% TFA in acetonitrile (solvent B). After intact mass spectrometry, site occupancy (see Table 2) was calculated from peak abundances of non-glycosylated peaks versus peak abundances of peaks representing the glycovariant carrying a single GlcNAc residue after endoT digestion of yeast high mannose glycans.

TABLE 2

| | Insert | | | | *Pichia* | Site occupancy |
|---|---|---|---|---|---|---|
| Vector | N-terminal | GOI | Modification | C-terminal | strain | % |
| pKai61 | | GBP | WT | His6 | GSM5 | N/A |
| pKai61 | | GBP | Q14N-P15A-G16T | His6 | GSM5 | 95 |
| pKai61 | | GBP | G27N-P30T | His6 | GSM5 | 95 |
| ppExpr | EAEAGS | GBP | Q46N-P48T | GS-His8 | GSM5 | 14 |
| pKai61 | | GBP | P48N-K50T | His6 | GSM5 | 96 |
| ppExpr | EAEAGS | GBP | P48N-K50T | GS-His8 | GSM5 | 94 |
| ppExpr | EAEAGS | GBP | K50B-R52T | GS-His8 | GSM5 | 70 |
| pKai61 | | GBP | R86N | His6 | GSM5 | 82 |
| ppExpr | EAEAGS | GBP | K97N-P98A-E99T | GS-His8 | GSM5 | 74 |
| ppExpr | EAEAGS | GBP | E99N | GS-His8 | GSM5 | 71 |

N-glycosylation site occupancy of several GBP N-glycosylation variants. Variants expressed in the ppExpr vector carry an N-terminal EAEAGS tag (partially processed) and a C-terminal GS-Hs tag, whereas variants expressed in the pKai61 vector carry a C-terminal He tag. Pichia strain GSM5 = GlycoSwitchM5 (alternative name for the Pichia Kai3 strain). Site occupancy was determined by intact protein mass spectrometry after endoT digestion of the high-mannose N-glycans to a single GlcNAc.

Figure 4:
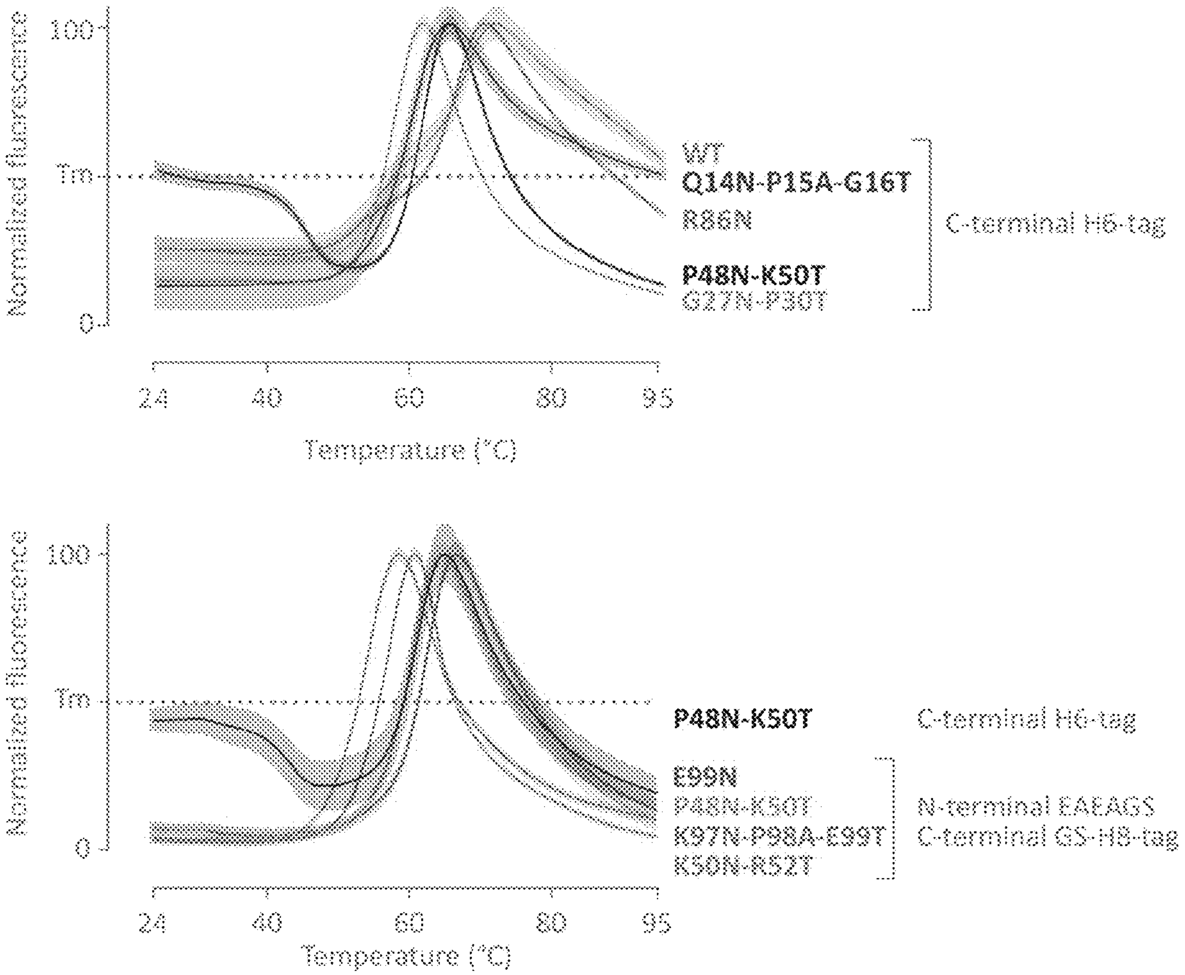
Figure 5:
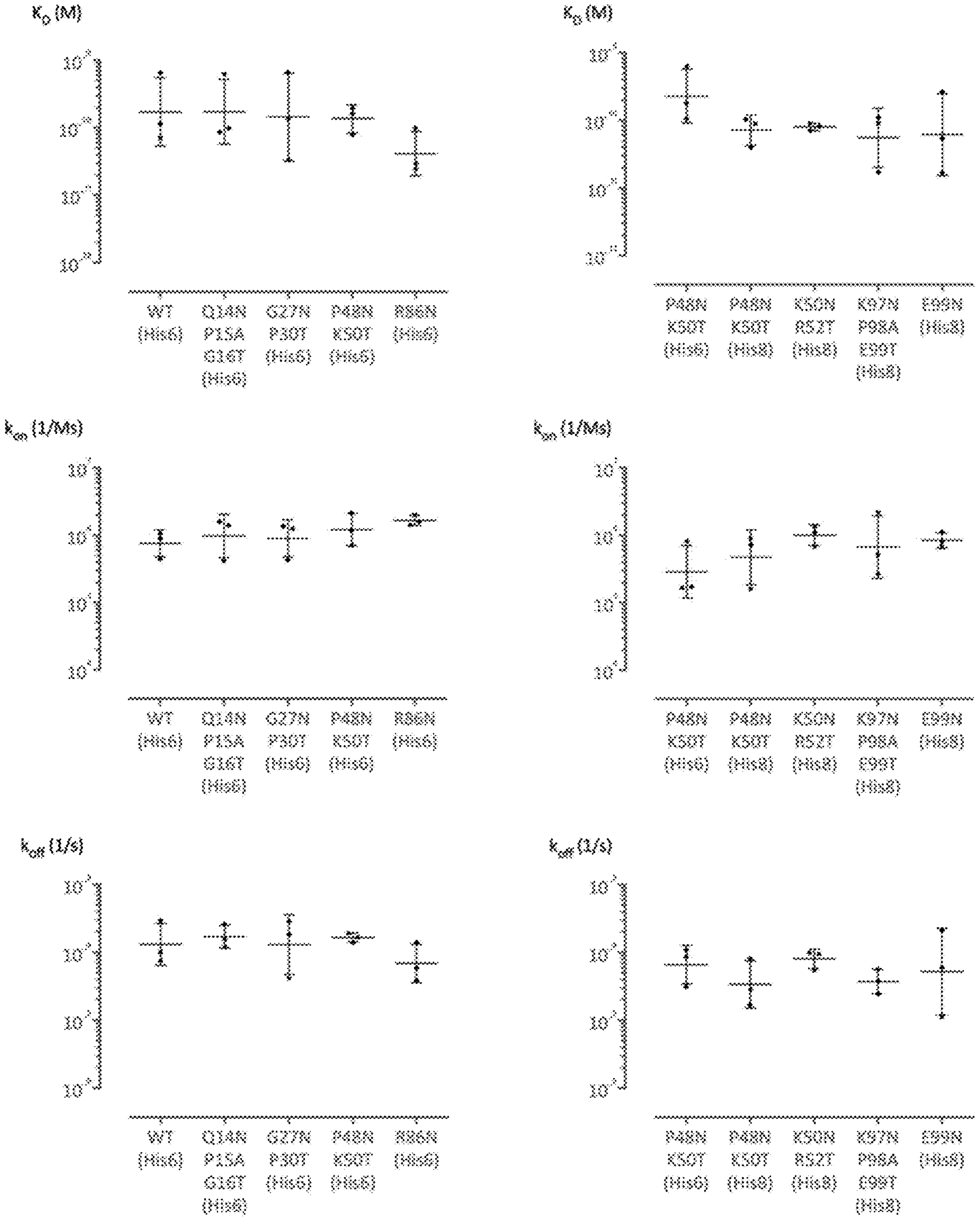
Figure 6:
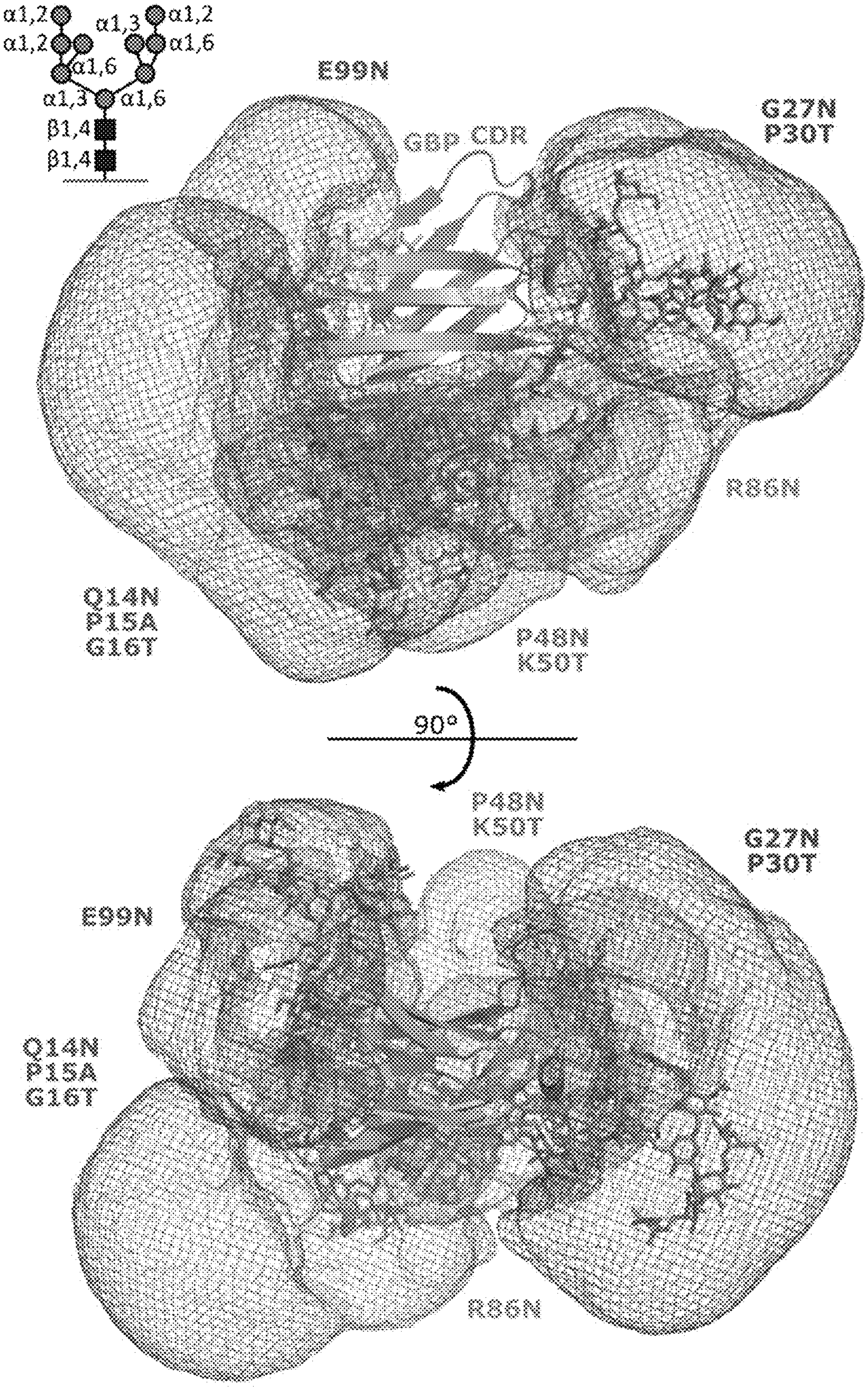
Figure 7:
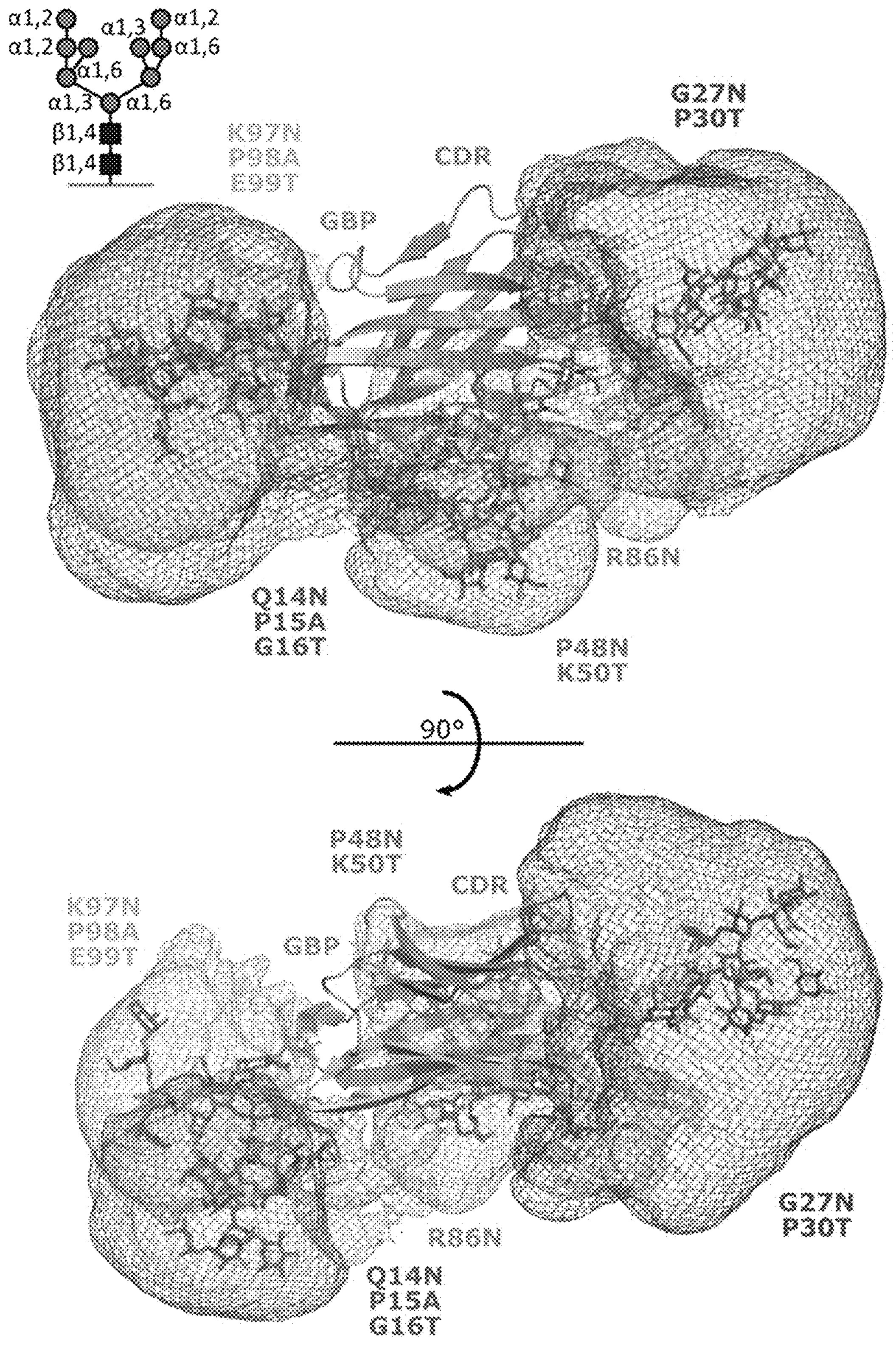
Figure 8:
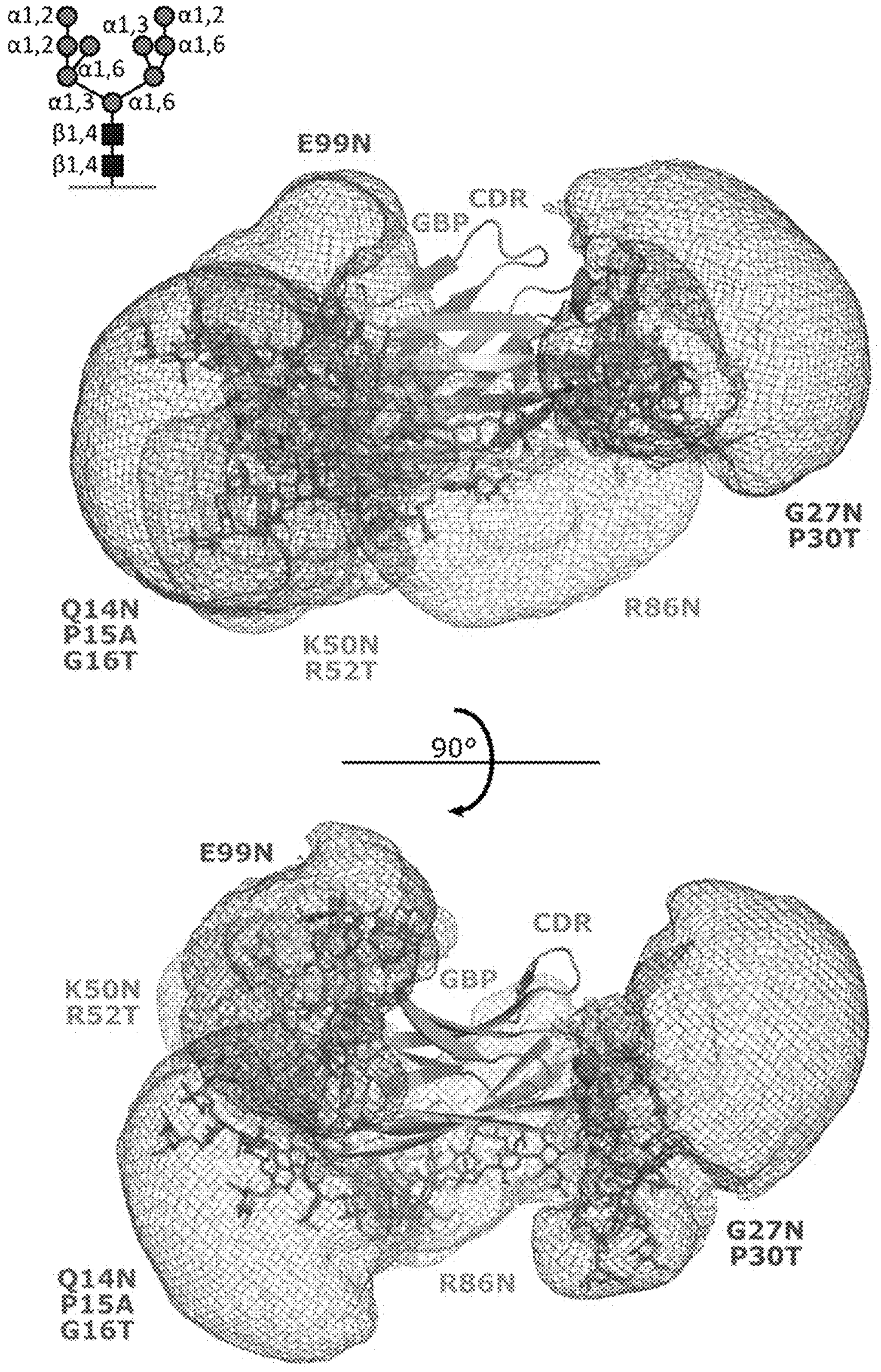
Figure 9:
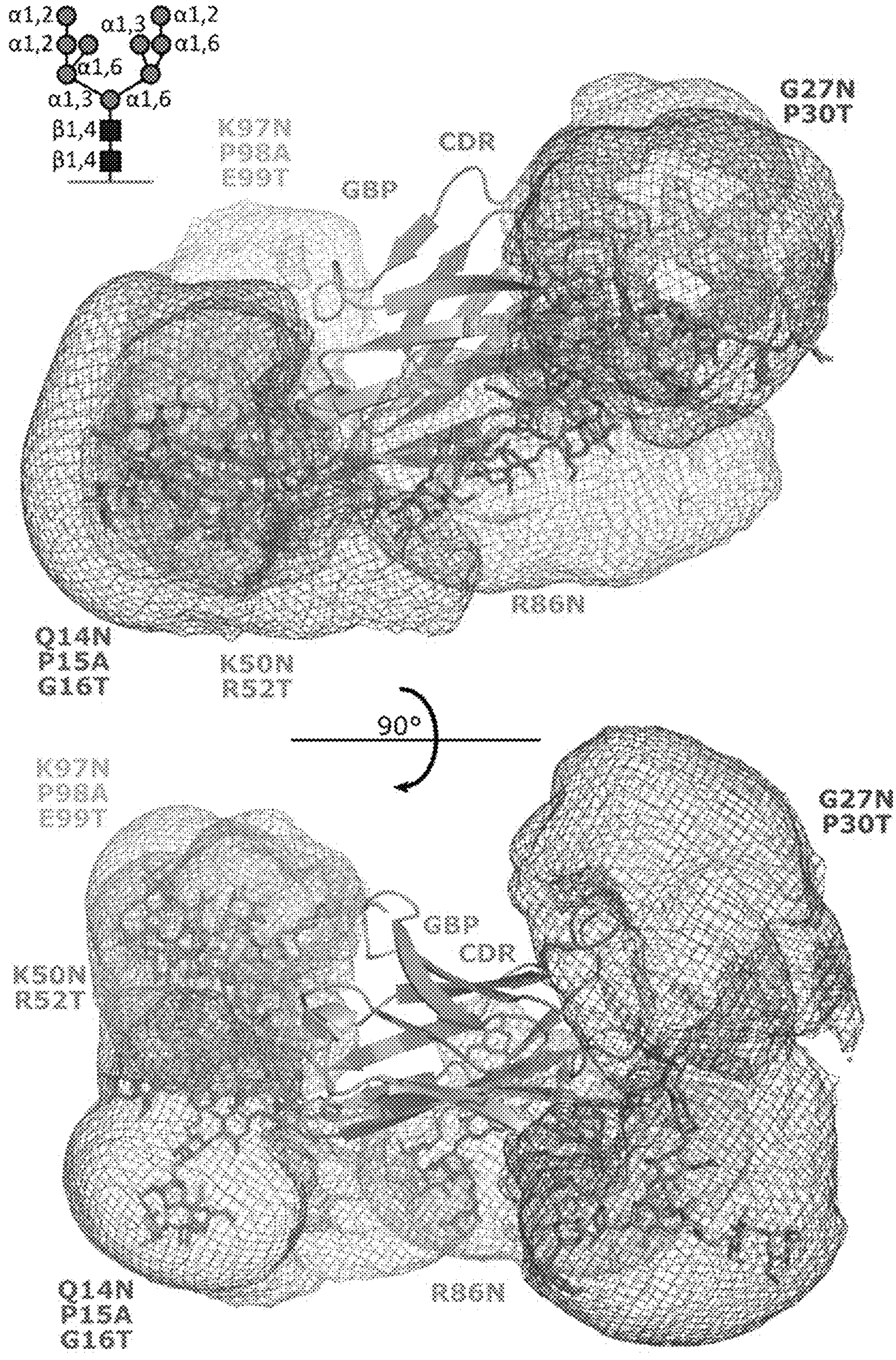

To verify whether nanobody functionality was retained, we analyzed thermal stability (FIG. 4) and GFP binding affinity (FIG. 5) of both unmodified GBP nanobody and the glyco-engineered GBP variants with a glycan at position 50, 97, and 99. Selected glycovariants were recombinantly produced in the *Pichia pastoris* GSM5 strain and purified via immobilized metal affinity chromatography and size exclusion chromatography. Melting curves of GBP-WT and its glycovariants were obtained in a thermal shift assay using SYPRO Orange dye in a qPCR machine (Huynh K & Partch C L in *Current Protocols in Protein Sciences* 79, 2015). Introduction of a $Man_5GlcNAc_2$ type N-glycan at position 50, 97 or 99 changed the melting curve shape (only one denaturation peak instead of the two denaturation peaks observed for GBP-WT), but had limited effect on the temperature at which thermal denaturation is initiated.

Biolayer interferometry assesing binding to biotinylated AviTag-GFP immobilized to ForteBio streptavidin biosensors (see FIG. 5) showed that the presence of an N-glycan at the 3 specified sites did not impair antigen binding: GFP binding affinity is in the sub-nanomolar range.

4. Experimental Validation of the Selected N-Glycosylation Sites into the AS26 Nanobody The rationally designed and proposed N-glycosylation acceptor sites specified in Example 2 were introduced into the AS26 nanobody. All the AS26 variants were equipped with a C-terminal histidine-tag (8×HIS) which facilitates purification and/or detection. As a result of the cloning methodology, a GS linker was introduced N-terminally.

The amino acid sequence of wild type VHH AS26 is depicted in SEQ ID NO: 9
GSEVQLVESGGGLVQAGGSLRLSCAASGRNIKEYVMGWFRQAPGKEREFVA

AISWSAGNIYYADSVKGRFTISRDNAKNTVHLQMNTLRPEDTAVYYCAAGR

YSAWYVAAYEYDYWGQGTQVTVSSHHHHHH

The aminoterminal GS is a scar from the cloning method. The C-terminal HisTag (6x) was introduced for purification reasons.

SEQ ID NO: 10 depicts that AS26 amino acid sequence with the N14 neo-N-glycan site (in bold):
GSEVQLVESGGGLVNATGSLRLSCAASGRNIKEYVMGWFRQAPGKEREFVA

AISWSAGNIYYADSVKGRFTISRDNAKNTVHLQMNTLRPEDTAVYYCAAGR

YSAWYVAAYEYDYWGQGTQVTVSSHHHHHH

SEQ ID NO: 11 depicts that AS26 amino acid sequence with the N27 neo-N-glycan site (in bold):
GSEVQLVESGGGLVQAGGSLRLSCAASNRTIKEYVMGWFRQAPGKEREFVA

AISWSAGNIYYADSVKGRFTISRDNAKNTVHLQMNTLRPEDTAVYYCAAGR

YSAWYVAAYEYDYWGQGTQVTVSSHHHHHH

SEQ ID NO: 12 depicts that AS26 amino acid sequence with the N86 neo-N-glycan site (in bold):
GSEVQLVESGGGLVQAGGSLRLSCAASGRNIKEYVMGWFRQAPGKEREFVA

AISWSAGNIYYADSVKGRFTISRDNANNTVHLQMNTLRPEDTAVYYCAAGR

YSAWYVAAYEYDYWGQGTQVTVSSHHHHHH

SEQ ID NO: 13 depicts that AS26 amino acid sequence with the N97 neo-N-glycan site (in bold):
GSEVQLVESGGGLVQAGGSLRLSCAASGRNIKEYVMGWFRQAPGKEREFVA

AISWSAGNIYYADSVKGRFTISRDNAKNTVHLQMNTLNATDTAVYYCAAGR

YSAWYVAAYEYDYWGQGTQVTVSSHHHHHH

-continued

SEQ ID NO: 14 depicts that AS26 amino acid sequence with the N99 neo-N-glycan site (in bold):
GSEVQLVESGGGLVQAGGSLRLSCAASGRNIKEYVMGWFRQAPGKEREFVA

AISWSAGNIYYADSVKGRFTISRDNAKNTVHLQMNTLRPNDTAVYYCAAGR

YSAWYVAAYEYDYWGQGTQVTVSSHHHHHH

The coding sequences of the wild type AS26 nanobody and the different mutants with introduced N-glycosylation acceptor sites in specific positions were operably linked to the AOX1 promoter (a methanol inducible promoter) of *Pichia pastoris*. The resulting expression vectors were introduced in the GlycoDelete strain of *Pichia pastoris*, modified with galactostyltransferase, resulting in glycoproteins with GlcNAc or LacNAc glycans. The different recombinant *Pichia pastoris* cultures were then first grown in medium containing glycerol as the sole carbon source for 48 h at 28° C., and subsequently recombinant protein expression was induced by substitution of glycerol for methanol. After another 48 hours at 28° C., the growth medium (supernatant) was collected of each recombinant culture. Subsequently, the glycan composition of each AS26 nanobody variant was analyzed by MS. Results of this analysis are shown in Table 3. Our data shows that glycosylation of nanobody AS26 could be obtained for all the glycovariants albeit with varying efficiency of N-glycosylation. Variants at position 97, 86 and 99 show an exceptionally high glycan occupancy. At position 14 the glycan position is high, while at position 27 the glycan occupancy is only 30 percent. Positions 14, 27, 86, 97 and 99 are according to the AHo numbering.

TABLE 3

| Nanobody N-glycan site | No N-glycan | GlcNAc | LacNAc |
|---|---|---|---|
| N14 | 13 | 20 | 67 |
| N27 | 68 | 14 | 18 |
| N86 | 6.3 | 33 | 60.7 |
| N97 | 2 | 28 | 70 |
| N99 | 7 | 71 | 22 |

the glycan composition of each variant AS26 nanobody was analyzed by MS. The % of occurrence of no N-glycan, a GlcNAc residue or a LacNAc residue on each of these introduced N-glycan sites is shown.

5. Use of Molecular Dynamics Simulations to Map the Glycans on Glyco-Engineered ISVDs (Newly Identified Glycosylation Sites)

To get an idea of the general orientation and space occupancy of glycans appended to the newly identified preferred glycosylation sites, we performed a second round of molecular dynamics simulations where we simulated the space occupancy of glycans appended at site 50, 97, and 99 (new sites) in different combinations with sites 14, 27, 48, and 86 (previously identified sites). Molecular dynamics simulations suggest that glycan chains at these new sites are projected away from the antigen-binding region, minimizing the risk of interfering with antigen recognition (see FIGS. 6, 7, 8 and 9).

The invention claimed is:

1. A polynucleotide encoding a polypeptide, wherein the encoded polypeptide comprises:

an immunoglobulin single variable domain (ISVD) derived from a camelid heavy chain antibody and having the same antigen specificity as the camelid heavy chain antibody from which it is derived, wherein the ISVD comprises an amino acid sequence that comprises 4 framework regions (FR) and 3 complementarity determining regions (CDR) according to the following formula (1): FR1-CDR1-FR2-CDR2-FR3-CDR3-FR4 (1), and wherein the ISVD contains an NXT, NXS, NXC or NXV motif, in which X can be any amino acid, such that the asparagine residue of the NXT/NXS/NXC/NXV motif is present at an amino acid selected from positions 50 and/or 52 of the ISVD according to the AHo numbering convention.

2. An expression vector comprising the polynucleotide of claim 1.

3. A cell comprising the expression vector of claim 2.

4. The cell of claim 3, wherein the cell is a higher eukaryotic cell, a mammalian cell, a plant cell, a lower eukaryotic cell, a filamentous fungus cell, a yeast cell, or a prokaryotic cell.

5. The cell of claim 3, wherein the cell is a glyco-engineered cell.

6. The cell of claim 5, wherein the polypeptide is expressed in the cell and is glycosylated and comprises one or more glycans, wherein the glycans have a terminal GlcNAc, GalNAc, Galactose, Sialic Acid, Glucose, Glucosamine, Galactosamine, Bacillosamine, Mannose, or Mannose-6-P sugar, GalNAz, GlcNAz, azido-sialic acid, or a chemically modified monosaccharide.

7. The cell of claim 5, wherein the polypeptide is expressed in the cell and is glycosylated and wherein the glycosylation of the polypeptide consists of one or more glycans selected from the group consisting of GlcNAc, LacNAc, sialyl-LacNAc, Man5GlcNAc2, Man8GlcNAc2, Man9GlcNAc2, Man10GlcNAc2, hyper-mannosylated glycans, mannose-6-phosphate glycans, complex glycans, and hybrid glycans.

8. A composition comprising the polynucleotide of claim 1, wherein the composition further comprises a pharmaceutical excipient.

9. The polynucleotide of claim 1, wherein the ISVD has at least one secondary glycosylation acceptor site at a location selected from the amino acids at positions 83 to 88 and/or the amino acids at positions 27 to 40 and/or amino acid position 14 and/or 48 and/or 103 according to AHo numbering convention.

* * * * *

SEQUENCE LISTING

```
<160> NUMBER OF SEQ ID NOS: 21

<210> SEQ ID NO 1
<211> LENGTH: 121
<212> TYPE: PRT
<213> ORGANISM: Artificial Sequence
<220> FEATURE:
```

```
<223> OTHER INFORMATION: Nanobody GBP

<400> SEQUENCE: 1

Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
                85                  90                  95

Asn Val Asn Val Gly Phe Glu Tyr Trp Gly Gln Gly Thr Gln Val Thr
            100                 105                 110

Val Ser Ser His His His His His His
        115                 120


<210> SEQ ID NO 2
<211> LENGTH: 8
<212> TYPE: PRT
<213> ORGANISM: Artificial Sequence
<220> FEATURE:
<223> OTHER INFORMATION: CDR1

<400> SEQUENCE: 2

Gly Phe Pro Val Asn Arg Tyr Ser
1               5


<210> SEQ ID NO 3
<211> LENGTH: 9
<212> TYPE: PRT
<213> ORGANISM: Artificial Sequence
<220> FEATURE:
<223> OTHER INFORMATION: CDR2

<400> SEQUENCE: 3

Met Ser Ser Ala Gly Asp Arg Ser Ser
1               5


<210> SEQ ID NO 4
<211> LENGTH: 7
<212> TYPE: PRT
<213> ORGANISM: Artificial Sequence
<220> FEATURE:
<223> OTHER INFORMATION: CDR3

<400> SEQUENCE: 4

Asn Val Asn Val Gly Phe Glu
1               5


<210> SEQ ID NO 5
<211> LENGTH: 25
<212> TYPE: PRT
<213> ORGANISM: Artificial Sequence
<220> FEATURE:
<223> OTHER INFORMATION: FR1

<400> SEQUENCE: 5

Gln Val Gln Leu Val Glu Ser Gly Gly Ala Leu Val Gln Pro Gly Gly
1               5                   10                  15
```

```
Ser Leu Arg Leu Ser Cys Ala Ala Ser
            20                  25


<210> SEQ ID NO 6
<211> LENGTH: 17
<212> TYPE: PRT
<213> ORGANISM: Artificial Sequence
<220> FEATURE:
<223> OTHER INFORMATION: FR2

<400> SEQUENCE: 6

Met Arg Trp Tyr Arg Gln Ala Pro Gly Lys Glu Arg Glu Trp Val Ala
1               5                   10                  15

Gly


<210> SEQ ID NO 7
<211> LENGTH: 37
<212> TYPE: PRT
<213> ORGANISM: Artificial Sequence
<220> FEATURE:
<223> OTHER INFORMATION: FR3

<400> SEQUENCE: 7

Tyr Glu Asp Ser Val Lys Gly Arg Phe Thr Ile Ser Arg Asp Asp Ala
1               5                   10                  15

Arg Asn Thr Val Tyr Leu Gln Met Asn Ser Leu Lys Pro Glu Asp Thr
            20                  25                  30

Ala Val Tyr Tyr Cys
        35


<210> SEQ ID NO 8
<211> LENGTH: 12
<212> TYPE: PRT
<213> ORGANISM: Artificial Sequence
<220> FEATURE:
<223> OTHER INFORMATION: FR4

<400> SEQUENCE: 8

Tyr Trp Gly Gln Gly Thr Gln Val Thr Val Ser Ser
1               5                   10


<210> SEQ ID NO 9
<211> LENGTH: 132
<212> TYPE: PRT
<213> ORGANISM: Artificial Sequence
<220> FEATURE:
<223> OTHER INFORMATION: VHH AS26

<400> SEQUENCE: 9

Gly Ser Glu Val Gln Leu Val Glu Ser Gly Gly Gly Leu Val Gln Ala
1               5                   10                  15

Gly Gly Ser Leu Arg Leu Ser Cys Ala Ala Ser Gly Arg Asn Ile Lys
            20                  25                  30

Glu Tyr Val Met Gly Trp Phe Arg Gln Ala Pro Gly Lys Glu Arg Glu
        35                  40                  45

Phe Val Ala Ala Ile Ser Trp Ser Ala Gly Asn Ile Tyr Tyr Ala Asp
    50                  55                  60

Ser Val Lys Gly Arg Phe Thr Ile Ser Arg Asp Asn Ala Lys Asn Thr
65                  70                  75                  80

Val His Leu Gln Met Asn Thr Leu Arg Pro Glu Asp Thr Ala Val Tyr
                85                  90                  95
```

```
Tyr Cys Ala Ala Gly Arg Tyr Ser Ala Trp Tyr Val Ala Ala Tyr Glu
            100                 105                 110

Tyr Asp Tyr Trp Gly Gln Gly Thr Gln Val Thr Val Ser Ser His His
        115                 120                 125

His His His His
    130


<210> SEQ ID NO 10
<211> LENGTH: 132
<212> TYPE: PRT
<213> ORGANISM: Artificial Sequence
<220> FEATURE:
<223> OTHER INFORMATION: AS26 amino acid sequence with the N14
      neo-N-glycan site

<400> SEQUENCE: 10

Gly Ser Glu Val Gln Leu Val Glu Ser Gly Gly Gly Leu Val Asn Ala
1               5                   10                  15

Thr Gly Ser Leu Arg Leu Ser Cys Ala Ala Ser Gly Arg Asn Ile Lys
            20                  25                  30

Glu Tyr Val Met Gly Trp Phe Arg Gln Ala Pro Gly Lys Glu Arg Glu
        35                  40                  45

Phe Val Ala Ala Ile Ser Trp Ser Ala Gly Asn Ile Tyr Tyr Ala Asp
    50                  55                  60

Ser Val Lys Gly Arg Phe Thr Ile Ser Arg Asp Asn Ala Lys Asn Thr
65                  70                  75                  80

Val His Leu Gln Met Asn Thr Leu Arg Pro Glu Asp Thr Ala Val Tyr
                85                  90                  95

Tyr Cys Ala Ala Gly Arg Tyr Ser Ala Trp Tyr Val Ala Ala Tyr Glu
            100                 105                 110

Tyr Asp Tyr Trp Gly Gln Gly Thr Gln Val Thr Val Ser Ser His His
        115                 120                 125

His His His His
    130


<210> SEQ ID NO 11
<211> LENGTH: 132
<212> TYPE: PRT
<213> ORGANISM: Artificial Sequence
<220> FEATURE:
<223> OTHER INFORMATION: AS26 amino acid sequence with the N27
      neo-N-glycan site

<400> SEQUENCE: 11

Gly Ser Glu Val Gln Leu Val Glu Ser Gly Gly Gly Leu Val Gln Ala
1               5                   10                  15

Gly Gly Ser Leu Arg Leu Ser Cys Ala Ala Ser Asn Arg Thr Ile Lys
            20                  25                  30

Glu Tyr Val Met Gly Trp Phe Arg Gln Ala Pro Gly Lys Glu Arg Glu
        35                  40                  45

Phe Val Ala Ala Ile Ser Trp Ser Ala Gly Asn Ile Tyr Tyr Ala Asp
    50                  55                  60

Ser Val Lys Gly Arg Phe Thr Ile Ser Arg Asp Asn Ala Lys Asn Thr
65                  70                  75                  80

Val His Leu Gln Met Asn Thr Leu Arg Pro Glu Asp Thr Ala Val Tyr
                85                  90                  95

Tyr Cys Ala Ala Gly Arg Tyr Ser Ala Trp Tyr Val Ala Ala Tyr Glu
            100                 105                 110
```

```
Tyr Asp Tyr Trp Gly Gln Gly Thr Gln Val Thr Val Ser Ser His His
        115                 120                 125

His His His His
    130


<210> SEQ ID NO 12
<211> LENGTH: 132
<212> TYPE: PRT
<213> ORGANISM: Artificial Sequence
<220> FEATURE:
<223> OTHER INFORMATION: AS26 amino acid sequence with the N86
      neo-N-glycan site

<400> SEQUENCE: 12

Gly Ser Glu Val Gln Leu Val Glu Ser Gly Gly Gly Leu Val Gln Ala
1               5                   10                  15

Gly Gly Ser Leu Arg Leu Ser Cys Ala Ala Ser Gly Arg Asn Ile Lys
            20                  25                  30

Glu Tyr Val Met Gly Trp Phe Arg Gln Ala Pro Gly Lys Glu Arg Glu
        35                  40                  45

Phe Val Ala Ala Ile Ser Trp Ser Ala Gly Asn Ile Tyr Tyr Ala Asp
    50                  55                  60

Ser Val Lys Gly Arg Phe Thr Ile Ser Arg Asp Asn Ala Asn Asn Thr
65                  70                  75                  80

Val His Leu Gln Met Asn Thr Leu Arg Pro Glu Asp Thr Ala Val Tyr
                85                  90                  95

Tyr Cys Ala Ala Gly Arg Tyr Ser Ala Trp Tyr Val Ala Ala Tyr Glu
            100                 105                 110

Tyr Asp Tyr Trp Gly Gln Gly Thr Gln Val Thr Val Ser Ser His His
        115                 120                 125

His His His His
    130


<210> SEQ ID NO 13
<211> LENGTH: 132
<212> TYPE: PRT
<213> ORGANISM: Artificial Sequence
<220> FEATURE:
<223> OTHER INFORMATION: AS26 amino acid sequence with the N97
      neo-N-glycan site

<400> SEQUENCE: 13

Gly Ser Glu Val Gln Leu Val Glu Ser Gly Gly Gly Leu Val Gln Ala
1               5                   10                  15

Gly Gly Ser Leu Arg Leu Ser Cys Ala Ala Ser Gly Arg Asn Ile Lys
            20                  25                  30

Glu Tyr Val Met Gly Trp Phe Arg Gln Ala Pro Gly Lys Glu Arg Glu
        35                  40                  45

Phe Val Ala Ala Ile Ser Trp Ser Ala Gly Asn Ile Tyr Tyr Ala Asp
    50                  55                  60

Ser Val Lys Gly Arg Phe Thr Ile Ser Arg Asp Asn Ala Lys Asn Thr
65                  70                  75                  80

Val His Leu Gln Met Asn Thr Leu Asn Ala Thr Asp Thr Ala Val Tyr
                85                  90                  95

Tyr Cys Ala Ala Gly Arg Tyr Ser Ala Trp Tyr Val Ala Ala Tyr Glu
            100                 105                 110

Tyr Asp Tyr Trp Gly Gln Gly Thr Gln Val Thr Val Ser Ser His His
        115                 120                 125
```

His His His His
130

<210> SEQ ID NO 14
<211> LENGTH: 132
<212> TYPE: PRT
<213> ORGANISM: Artificial Sequence
<220> FEATURE:
<223> OTHER INFORMATION: AS26 amino acid sequence with the N99
neo-N-glycan site

<400> SEQUENCE: 14

```
Gly Ser Glu Val Gln Leu Val Glu Ser Gly Gly Gly Leu Val Gln Ala
1               5                   10                  15

Gly Gly Ser Leu Arg Leu Ser Cys Ala Ala Ser Gly Arg Asn Ile Lys
            20                  25                  30

Glu Tyr Val Met Gly Trp Phe Arg Gln Ala Pro Gly Lys Glu Arg Glu
        35                  40                  45

Phe Val Ala Ala Ile Ser Trp Ser Ala Gly Asn Ile Tyr Tyr Ala Asp
    50                  55                  60

Ser Val Lys Gly Arg Phe Thr Ile Ser Arg Asp Asn Ala Lys Asn Thr
65                  70                  75                  80

Val His Leu Gln Met Asn Thr Leu Arg Pro Asn Asp Thr Ala Val Tyr
                85                  90                  95

Tyr Cys Ala Ala Gly Arg Tyr Ser Ala Trp Tyr Val Ala Ala Tyr Glu
            100                 105                 110

Tyr Asp Tyr Trp Gly Gln Gly Thr Gln Val Thr Val Ser Ser His His
        115                 120                 125

His His His His
    130
```

<210> SEQ ID NO 15
<211> LENGTH: 4
<212> TYPE: PRT
<213> ORGANISM: Artificial Sequence
<220> FEATURE:
<223> OTHER INFORMATION: aromatic residue
<220> FEATURE:
<221> NAME/KEY: MISC_FEATURE
<222> LOCATION: (1)..(1)
<223> OTHER INFORMATION: X can be F, Y, H or W
<220> FEATURE:
<221> NAME/KEY: MISC_FEATURE
<222> LOCATION: (3)..(3)
<223> OTHER INFORMATION: X can be any amino acid except proline
<220> FEATURE:
<221> NAME/KEY: MISC_FEATURE
<222> LOCATION: (4)..(4)
<223> OTHER INFORMATION: X can be T or S

<400> SEQUENCE: 15

```
Xaa Asn Xaa Xaa
1
```

<210> SEQ ID NO 16
<211> LENGTH: 5
<212> TYPE: PRT
<213> ORGANISM: Artificial Sequence
<220> FEATURE:
<223> OTHER INFORMATION: aromatic residue
<220> FEATURE:
<221> NAME/KEY: MISC_FEATURE
<222> LOCATION: (1)..(1)
<223> OTHER INFORMATION: X can be F, Y, H or W
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (4)..(4)
<223> OTHER INFORMATION: X can be any amino acid except proline
<220> FEATURE:
<221> NAME/KEY: MISC_FEATURE
<222> LOCATION: (5)..(5)
<223> OTHER INFORMATION: X can be T or S

<400> SEQUENCE: 16

Xaa Xaa Asn Xaa Xaa
1               5

<210> SEQ ID NO 17
<211> LENGTH: 6
<212> TYPE: PRT
<213> ORGANISM: Artificial Sequence
<220> FEATURE:
<223> OTHER INFORMATION: aromatic residue
<220> FEATURE:
<221> NAME/KEY: MISC_FEATURE
<222> LOCATION: (1)..(1)
<223> OTHER INFORMATION: X can F, Y, H or W
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid except proline
<220> FEATURE:
<221> NAME/KEY: MISC_FEATURE
<222> LOCATION: (6)..(6)
<223> OTHER INFORMATION: X can be T or S

<400> SEQUENCE: 17

Xaa Xaa Xaa Asn Xaa Xaa
1               5

<210> SEQ ID NO 18
<211> LENGTH: 5
<212> TYPE: PRT
<213> ORGANISM: Artificial Sequence
<220> FEATURE:
<223> OTHER INFORMATION: aromatic residue
<220> FEATURE:
<221> NAME/KEY: MISC_FEATURE
<222> LOCATION: (4)..(4)
<223> OTHER INFORMATION: X can be any amino acid except proline

<400> SEQUENCE: 18

Gly Gly Asn Xaa Thr
1               5

<210> SEQ ID NO 19
<211> LENGTH: 4
<212> TYPE: PRT
<213> ORGANISM: Artificial Sequence
<220> FEATURE:
<223> OTHER INFORMATION: aromatic residue
<220> FEATURE:
<221> NAME/KEY: MISC_FEATURE
<222> LOCATION: (3)..(3)
<223> OTHER INFORMATION: X can be any amino acid except proline

<400> SEQUENCE: 19

```
Gly Asn Xaa Thr
1


<210> SEQ ID NO 20
<211> LENGTH: 4
<212> TYPE: PRT
<213> ORGANISM: Artificial Sequence
<220> FEATURE:
<223> OTHER INFORMATION: aromatic residue
<220> FEATURE:
<221> NAME/KEY: MISC_FEATURE
<222> LOCATION: (2)..(2)
<223> OTHER INFORMATION: X can be any amino acid except proline

<400> SEQUENCE: 20

Asn Xaa Thr Gly
1


<210> SEQ ID NO 21
<211> LENGTH: 5
<212> TYPE: PRT
<213> ORGANISM: Artificial Sequence
<220> FEATURE:
<223> OTHER INFORMATION: aromatic residue
<220> FEATURE:
<221> NAME/KEY: MISC_FEATURE
<222> LOCATION: (2)..(2)
<223> OTHER INFORMATION: X can be any amino acid except proline

<400> SEQUENCE: 21

Asn Xaa Thr Gly Gly
1               5
```